US008200507B2

(12) United States Patent
Kanada et al.

(10) Patent No.: US 8,200,507 B2
(45) Date of Patent: Jun. 12, 2012

(54) EXAMINATION INFORMATION MANAGEMENT APPARATUS

(76) Inventors: Shouji Kanada, Minato-ku (JP);
Takahiro Ito, Minato-ku (JP);
Yoshifumi Shioe, Minato-ku (JP)

( * ) Notice: Subject to any disclaimer, the term of this patent is extended or adjusted under 35 U.S.C. 154(b) by 583 days.

(21) Appl. No.: 11/766,451

(22) Filed: Jun. 21, 2007

(65) Prior Publication Data

US 2008/0044800 A1    Feb. 21, 2008

(30) Foreign Application Priority Data

Jun. 28, 2006  (JP) ................................. 2006-177781

(51) Int. Cl.
*G06Q 50/00* (2012.01)
(52) U.S. Cl. ............................................................ 705/3
(58) Field of Classification Search ....................... 705/3
See application file for complete search history.

(56) References Cited

U.S. PATENT DOCUMENTS

| 5,779,634 | A | * | 7/1998 | Ema et al. ...................... 600/407 |
| 5,807,256 | A | * | 9/1998 | Taguchi et al. ................ 600/425 |
| 6,381,557 | B1 | * | 4/2002 | Babula et al. ................. 702/183 |

FOREIGN PATENT DOCUMENTS

| JP | 5-282384 A | 10/1993 |
| JP | 2001-331581 A | 11/2001 |
| JP | 2002-109071 A | 4/2002 |
| JP | 2003-199716 A | 7/2003 |
| JP | 2003-281273 A | 10/2003 |

OTHER PUBLICATIONS

Japanese Office Action corresponding to Japanese Patent Application No. 2006-177781, dated Feb. 22, 2011.

* cited by examiner

*Primary Examiner* — Gerald J. O'Connor
*Assistant Examiner* — Hiep V Nguyen
(74) *Attorney, Agent, or Firm* — Sughrue Mion, PLLC

(57) ABSTRACT

An examination information management apparatus that enables a client doctor to select a more proper examination. The apparatus includes a hard disk for storing a database that accumulates information on evaluations of examinations performed for predicted disease names, an examination information managing unit for managing the database, an examination request prior information acquiring unit for acquiring examination request prior information including information representing a predicted disease name and an examination candidate, and causing the examination information managing unit to perform search in the database based on the examination request prior information, an examination content judging unit for acquiring information on an evaluation of the examination candidate for the predicted disease name based on the search performed by the examination information managing unit, and an examination content validity outputting unit for outputting the information on the evaluation acquired by the examination content judging unit to a client doctor terminal.

4 Claims, 34 Drawing Sheets

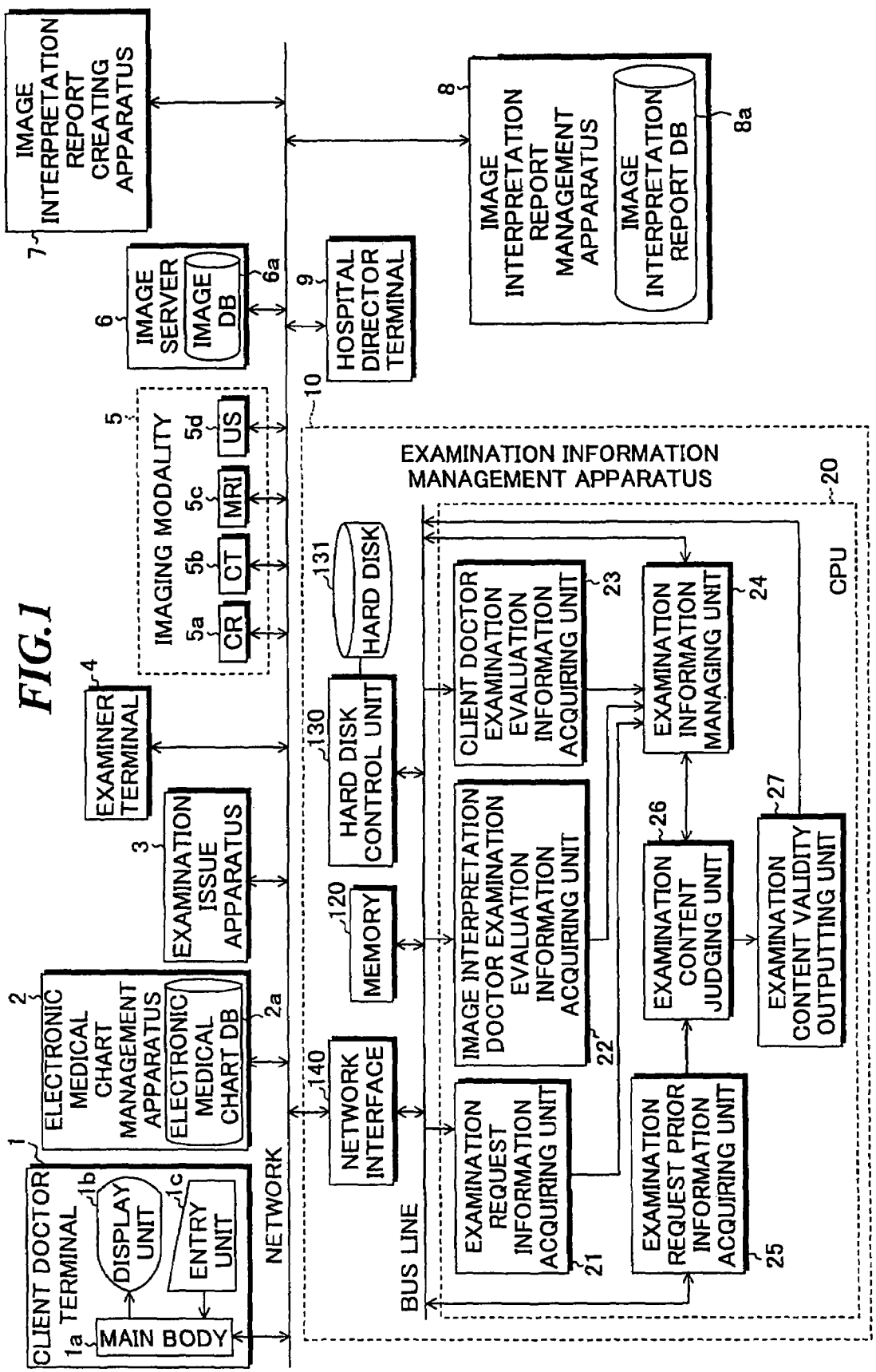

FIG.2

EXAMINATION REQUEST INFORMATION DB

| IMAGE INTERPRETATION REPORT ID | CLIENT DOCTOR NAME | EXAMINATION ID | EXAMINATION TYPE | EXAMINATION CONTENT | PREDICTED DISEASE NAME | PRIOR CERTAINTY FACTOR |
|---|---|---|---|---|---|---|
| 123456 | Tanaka Ichiro | US0001 | US | ABDOMINAL US | FATTY LIVER | 3 |
| 100001 | Suzuki Jiro | US0002 | US | ABDOMINAL US | FATTY LIVER | 2 |
| 100002 | Suzuki Jiro | CT0001 | CT | ABDOMINAL CT | CIRRHOSIS | 3 |
| 200001 | Suzuki Jiro | CT0002 | CT | ABDOMINAL CT | LIVER CANCER | 3 |
| 200002 | Suzuki Jiro | CT0003 | CT | ABDOMINAL CT | CIRRHOSIS | 1 |
| 200003 | Suzuki Jiro | ZCT001 | CONTRAST CT | ABDOMINAL CT CONTRAST | CIRRHOSIS | 1 |
| 200004 | Tanaka Ichiro | US0003 | US | ABDOMINAL US | CIRRHOSIS | 2 |
| 200005 | Tanaka Ichiro | CT0004 | CT | ABDOMINAL CT | FATTY LIVER | 2 |
| 200006 | Tanaka Ichiro | MRI001 | MRI | ABDOMINAL MRI | FATTY LIVER | 1 |
| ... | ... | ... | ... | ... | ... | ... |

FIG.3

IMAGE INTERPRETATION DOCTOR EXAMINATION EVALUATION INFORMATION DB

| IMAGE INTERPRETATION REPORT ID | FINDING | IMAGE INTERPRETATION DOCTOR DIAGNOSIS | IMAGE INTERPRETATION DOCTOR NAME | PROPERNESS FACTOR OF REQUESTED CONTENT | CERTAINTY FACTOR OF IMAGE INTERPRETATION RESULT |
|---|---|---|---|---|---|
| 123456 | LIVER KIDNEY CONTRAST HIGH | FATTY LIVER | Fuji Taro | 3 | 3 |
| 100001 | ... | HEPATITIS | Fuji Kuroto | 1 | 2 |
| 100002 | ... | LIVER CANCER | Fuji Kuroto | 2 | 3 |
| 200001 | ... | LIVER CANCER | Fuji Taro | 3 | 3 |
| 200002 | ... | CIRRHOSIS | Fuji Taro | 1 | 3 |
| 200003 | ... | CIRRHOSIS | Fuji Taro | 1 | 3 |
| 200004 | ... | CIRRHOSIS | Fuji Kuroto | 3 | 3 |
| 200005 | ... | FATTY LIVER | Fuji Kuroto | 2 | 2 |
| 200006 | ... | FATTY LIVER | Fuji Kuroto | 1 | 1 |
| ... | ... | ... | ... | ... | ... |

FIG.4

CLIENT DOCTOR EXAMINATION EVALUATION INFORMATION DB

| IMAGE INTERPRETATION REPORT ID | EFFECTIVENESS FACTOR OF IMAGE INTERPRETATION RESULT |
|---|---|
| 123456 | 2 |
| 100001 | 3 |
| 100002 | 3 |
| 200001 | 2 |
| 200002 | 2 |
| 200003 | 2 |
| 200004 | 3 |
| 200005 | 3 |
| 200006 | 1 |
| ... | ... |

FIG.5

EXAMINATION VALIDITY EVALUATION INFORMATION DB

| PREDICTED DISEASE NAME | PRIOR CERTAINTY FACTOR | EXAMINATION CONTENT | PROPERNESS FACTOR OF REQUESTED CONTENT (AVERAGE VALUE) | CERTAINTY FACTOR OF IMAGE INTERPRETATION RESULT (AVERAGE VALUE) | EFFECTIVENESS FACTOR OF IMAGE INTERPRETATION RESULT (AVERAGE VALUE) |
|---|---|---|---|---|---|
| FATTY LIVER | 3 | ABDOMINAL US | 2.8 | 2.6 | 2.9 |
| FATTY LIVER | 3 | ABDOMINAL CT | 2.9 | 2.6 | 2.8 |
| FATTY LIVER | 3 | ABDOMINAL MRI | 1.2 | 1.2 | 1.8 |
| FATTY LIVER | 2 | ABDOMINAL US | 2.3 | 2.1 | 2.9 |
| FATTY LIVER | 2 | ABDOMINAL CT | 2.2 | 2.2 | 2.3 |
| FATTY LIVER | 2 | ABDOMINAL MRI | 1.2 | 1.3 | 1.6 |
| FATTY LIVER | 1 | ABDOMINAL US | 2.6 | 2.5 | 2.9 |
| FATTY LIVER | 1 | ABDOMINAL CT | 1.6 | 1.6 | 1.8 |
| FATTY LIVER | 1 | ABDOMINAL MRI | 1.1 | 1.2 | 1.5 |
| CIRRHOSIS | ... | ... | ... | ... | ... |
| ... | ... | ... | ... | ... | ... |

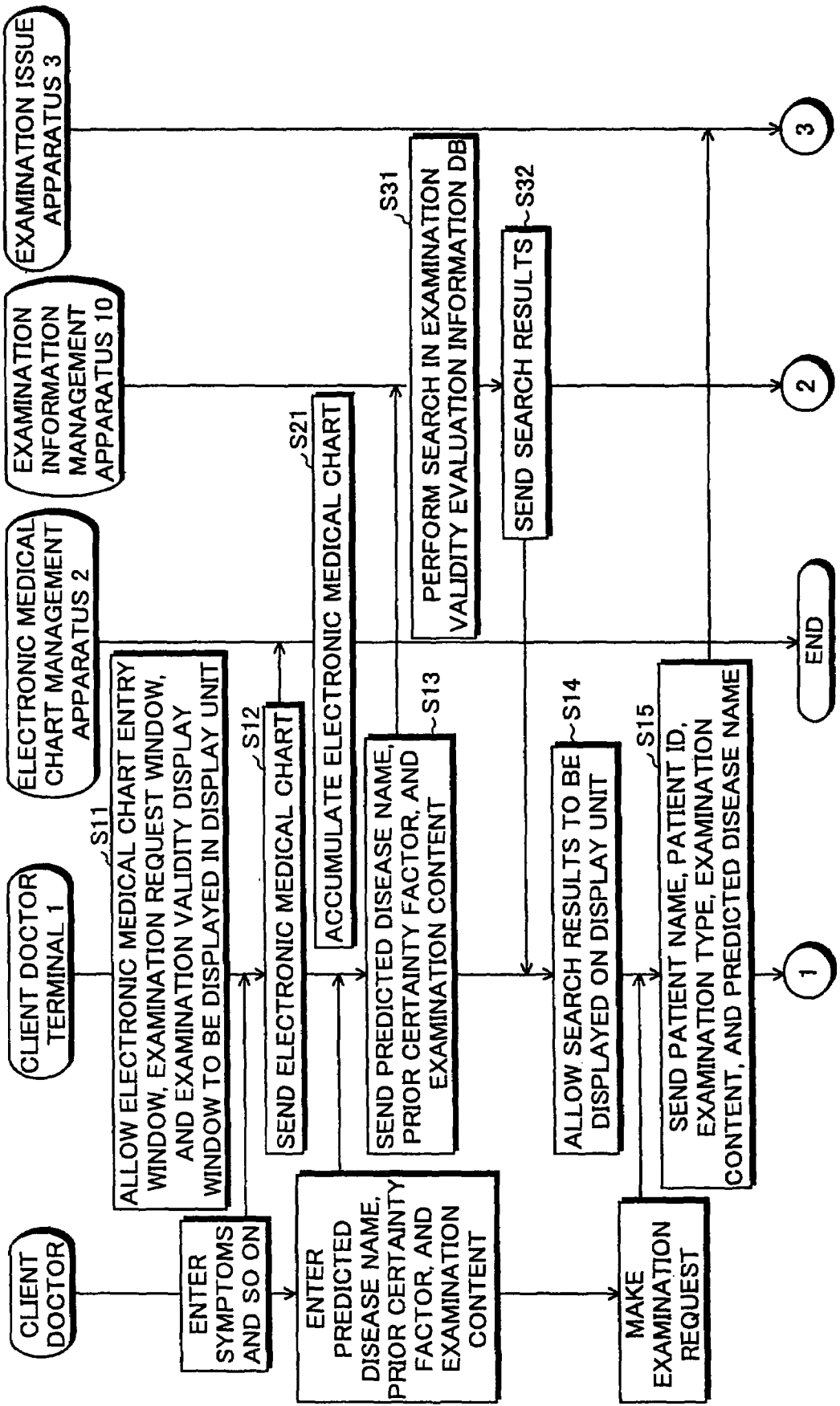

| MEDICAL RECORD || | 41 |||
|---|---|---|---|---|---|
| NUMBER OF PUBLIC FUND PROVIDER | | | INSURER NUMBER | | |
| RECIPIENT NUMBER OF PUBLIC FUNDED CARE | | | INSURANCE CARD INSURANCE CERTIFICATE |||

| CONSULTED PERSON | NAME | | | INSURED PERSON SIGN AND NUMBER | |
|---|---|---|---|---|---|
| | | | | EXPIRATION DATE YEAR MONTH DAY | |
| | | | | NAME OF INSURED PERSON | |
| | DATE OF BIRTH | YEAR MONTH DAY | MALE FEMALE | QUALIFICATION DATE | YEAR MONTH DAY |
| | | | ESTABLISHMENT (SHIP OWNER) | ADDRESS | |
| | ADDRESS | PHONE NUMBER | | PHONE NUMBER | |
| | | | INSURER | ADDRESS | |
| | OCCUPATION | | | PHONE NUMBER | |
| | RELATIONSHIP WITH INSURED PERSON | | | | |

| NAME OF DISEASE OR INJURY | DUTY | START DATE | END DATE | OUTCOME | EXPECTED EXPIRATION DATE |
|---|---|---|---|---|---|
| | DUTY NON-DUTY | YEAR MONTH DAY | YEAR MONTH DAY | HEALED DIED DISCONTINUED | YEAR MONTH DAY |
| | DUTY NON-DUTY | YEAR MONTH DAY | YEAR MONTH DAY | HEALED DIED DISCONTINUED | YEAR MONTH DAY |
| | DUTY NON-DUTY | YEAR MONTH DAY | YEAR MONTH DAY | HEALED DIED DISCONTINUED | YEAR MONTH DAY |

| NAME OF DISEASE OR INJURY | STATEMENT ON INCAPACITY || DURATION OF HOSPITALIZATION |
|---|---|---|---|
| | PERIOD OF INCAPACITY ENTERED IN STATEMENT | DATE OF DELIVERY OF STATEMENT | |
| | FROM MONTH DAY TO MONTH DAY   DAYS | YEAR MONTH DAY | FROM MONTH DAY TO MONTH DAY   DAYS |
| | FROM MONTH DAY TO MONTH DAY   DAYS | YEAR MONTH DAY | FROM MONTH DAY TO MONTH DAY   DAYS |

| IF OCCUPATION ACCIDENT OR COMMUTING ACCIDENT IS SUSPECTED, STATE THAT ||
|---|---|
| REMARKS | NUMBER OF PUBLIC FUND PROVIDER |
| | RECIPIENT NUMBER OF PUBLIC FUNDED CARE |

FIG.10

| PREVIOUS ILLNESSES, CAUSES, MAIN SYMPTOMS, AND SO ON | PRESCRIPTION, SURGERY, TREATMENT, AND SO ON |
|---|---|
| | |

( SAVE ELECTRONIC MEDICAL CHART ) — 51

42

EXAMINATION REQUEST — 43

PREDICTED DISEASE NAME [ ]

PRIOR CERTAINTY FACTOR [ ]
  3  HIGHLY POSSIBLE
  2  POSSIBLE
  1  UNDENIABLE

EXAMINATION CONTENT [ ]

( DISPLAY VALIDITY )

( REQUEST EXAMINATION )

EXAMINATION VALIDITY DISPLAY — 44

| PREVIOUS ILLNESSES, CAUSES, MAIN SYMPTOMS, AND SO ON | PRESCRIPTION, SURGERY, TREATMENT, AND SO ON |
|---|---|
| May 15, 2006, DOCTOR: Tanaka Ichiro<br>• MAJOR COMPLAINT<br>  LASSITUDE<br>  SWELLING<br>  JAUNDICE<br>• FINDING<br>  SUSPECTED TO HAVE<br>  FATTY LIVER | |

( SAVE ELECTRONIC MEDICAL CHART ) ~ 51

43

EXAMINATION REQUEST

PREDICTED DISEASE NAME [　　　]

PRIOR CERTAINTY FACTOR [　　　]
   3  HIGHLY POSSIBLE
   2  POSSIBLE
   1  UNDENIABLE

EXAMINATION CONTENT [　　　]

( DISPLAY VALIDITY )
( REQUEST EXAMINATION )

44

EXAMINATION VALIDITY DISPLAY

| PREVIOUS ILLNESSES, CAUSES, MAIN SYMPTOMS, AND SO ON | PRESCRIPTION, SURGERY, TREATMENT, AND SO ON |
|---|---|
| May 15, 2006, DOCTOR: Tanaka Ichiro<br>• MAJOR COMPLAINT<br>　LASSITUDE<br>　SWELLING<br>　JAUNDICE<br>• FINDING<br>　SUSPECTED TO HAVE<br>　FATTY LIVER | |

( SAVE ELECTRONIC MEDICAL CHART ) — 51

43

EXAMINATION REQUEST

| PREDICTED DISEASE NAME | FATTY LIVER | — 61 |
| PRIOR CERTAINTY FACTOR | 3 | — 62 |
| 　3　HIGHLY POSSIBLE<br>　2　POSSIBLE<br>　1　UNDENIABLE | | |
| EXAMINATION CONTENT | ABDOMINAL US | — 63 |

( DISPLAY VALIDITY ) — 64

( REQUEST EXAMINATION ) — 65

44

EXAMINATION VALIDITY DISPLAY

FIG.13

| PREVIOUS ILLNESSES, CAUSES, MAIN SYMPTOMS, AND SO ON | PRESCRIPTION, SURGERY, TREATMENT, AND SO ON |
|---|---|
| ·May 15, 2006, DOCTOR: Tanaka Ichiro<br>• MAJOR COMPLAINT<br>  LASSITUDE<br>  SWELLING<br>  JAUNDICE<br>• FINDING<br>  SUSPECTED TO HAVE<br>  FATTY LIVER | |

( SAVE ELECTRONIC MEDICAL CHART ) — 51

EXAMINATION REQUEST

PREDICTED DISEASE NAME: FATTY LIVER — 61

PRIOR CERTAINTY FACTOR: 3 — 62
  3 HIGHLY POSSIBLE
  2 POSSIBLE
  1 UNDENIABLE

EXAMINATION CONTENT: ABDOMINAL US — 63

( DISPLAY VALIDITY ) — 64
( REQUEST EXAMINATION ) — 65

EXAMINATION VALIDITY DISPLAY

| PREDICTED DISEASE NAME | PRIOR CERTAIN -TY FACTOR | EXAMINA -TION CONTENT | PROPER -NESS FACTOR OF REQUESTED CONTENT | CERTAINTY FACTOR OF IMAGE INTERPRE -TATION RESULT | EFFECTIVE -NESS FACTOR OF IMAGE INTERPRE -TATION RESULT |
|---|---|---|---|---|---|
| FATTY LIVER | 3 | ABDOMINAL US | 2.8 | 2.6 | 2.9 |
| FATTY LIVER | 3 | ABDOMINAL CT | 2.9 | 2.6 | 2.8 |
| FATTY LIVER | 3 | ABDOMINAL MRI | 1.2 | 1.2 | 1.8 |

FIG.14

EXAMINATION REQUEST INFORMATION DB

| IMAGE INTERPRETATION REPORT ID | CLIENT DOCTOR NAME | EXAMINATION ID | EXAMINATION TYPE | EXAMINATION CONTENT | PREDICTED DISEASE NAME | PRIOR CERTAINTY FACTOR |
|---|---|---|---|---|---|---|
| 123456 | Tanaka Ichiro | US0001 | US | ABDOMINAL US | FATTY LIVER | 3 |
| 100001 | Suzuki Jiro | US0002 | US | ABDOMINAL US | FATTY LIVER | 2 |
| 100002 | Suzuki Jiro | CT0001 | CT | ABDOMINAL CT | CIRRHOSIS | 3 |
| 200001 | Suzuki Jiro | CT0002 | CT | ABDOMINAL CT | LIVER CANCER | 3 |
| 200002 | Suzuki Jiro | CT0003 | CT | ABDOMINAL CT | CIRRHOSIS | 1 |
| 200003 | Suzuki Jiro | ZCT001 | CONTRAST CT | ABDOMINAL CT CONTRAST | CIRRHOSIS | 1 |
| 200004 | Tanaka Ichiro | US0003 | US | ABDOMINAL US | CIRRHOSIS | 2 |
| 200005 | Tanaka Ichiro | CT0004 | CT | ABDOMINAL CT | FATTY LIVER | 2 |
| 200006 | Tanaka Ichiro | MRI001 | MRI | ABDOMINAL MRI | FATTY LIVER | 1 |
| ... | ... | ... | ... | ... | ... | ... |
| 300001 | Tanaka Ichiro | US1001 | US | ABDOMINAL US | FATTY LIVER | 3 |

FIG.19

IMAGE INTERPRETATION DOCTOR EXAMINATION EVALUATION INFORMATION DB

| IMAGE INTERPRETATION REPORT ID | FINDING | IMAGE INTERPRETATION DOCTOR DIAGNOSIS | IMAGE INTERPRETATION DOCTOR NAME | PROPERNESS FACTOR OF REQUESTED CONTENT | CERTAINTY FACTOR OF IMAGE INTERPRETATION RESULT |
|---|---|---|---|---|---|
| 123456 | LIVER KIDNEY CONTRAST HIGH | FATTY LIVER | Fuji Taro | 3 | 3 |
| 100001 | ... | HEPATITIS | Fuji Kuroto | 1 | 2 |
| 100002 | ... | LIVER CANCER | Fuji Kuroto | 2 | 3 |
| 200001 | ... | LIVER CANCER | Fuji Taro | 3 | 3 |
| 200002 | ... | CIRRHOSIS | Fuji Taro | 1 | 3 |
| 200003 | ... | CIRRHOSIS | Fuji Taro | 1 | 3 |
| 200004 | ... | CIRRHOSIS | Fuji Kuroto | 3 | 3 |
| 200005 | ... | FATTY LIVER | Fuji Kuroto | 2 | 2 |
| 200006 | ... | FATTY LIVER | Fuji Kuroto | 1 | 1 |
| ... | ... | ... | ... | ... | ... |
| 300001 | LIVER KIDNEY CONTRAST HIGH | FATTY LIVER | Fuji Kuroto | 3 | 3 |

FIG.23

| PREVIOUS ILLNESSES, CAUSES, MAIN SYMPTOMS, AND SO ON | PRESCRIPTION, SURGERY, TREATMENT, AND SO ON |
|---|---|
| May 15, 2006, DOCTOR: Tanaka Ichiro<br>•MAJOR COMPLAINT<br>　LASSITUDE<br>　SWELLING<br>　JAUNDICE<br>•FINDING<br>　SUSPECTED TO HAVE<br>　FATTY LIVER<br>May 16, 2006, DOCTOR: Tanaka Ichiro<br>•DIAGNOSIS<br>　FATTY LIVER | |

( SAVE ELECTRONIC MEDICAL CHART ) ~51

42

---

IMAGE INTERPRETATION REPORT DISPLAY

EXAMINATION ID: US1001   EXAMINATION TYPE: US   PART: ABDOMEN ~101
PATIENT NAME: Yamada Saburo   SEX: MALE   AGE: 51
IMAGING DATE: May 15, 2006
COMMENTS: ○○○

FINDINGS: ~102
LIVER KIDNEY CONTRAST HIGH

IMAGE INTERPRETATION
DOCTOR DIAGNOSIS: FATTY LIVER  ~103

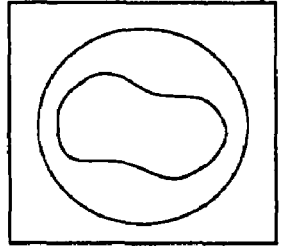

104

45

---

EXAMINATION EVALUATION ENTRY

EFFECTIVENESS OF
IMAGE INTERPRETATION  [ 3 ] ~111
RESULT
　3 IMAGE INTERPRETATION REPORT
　　WAS VERY USEFUL
　2 IMAGE INTERPRETATION REPORT
　　WAS USEFUL
　1 IMAGE INTERPRETATION REPORT
　　WAS USELESS 112
( SEND EXAMINATION EVALUATION )

CLIENT DOCTOR EXAMINATION EVALUATION INFORMATION DB

| IMAGE INTERPRETATION REPORT ID | EFFECTIVENESS FACTOR OF IMAGE INTERPRETATION RESULT |
|---|---|
| 123456 | 2 |
| 100001 | 3 |
| 100002 | 3 |
| 200001 | 2 |
| 200002 | 2 |
| 200003 | 2 |
| 200004 | 3 |
| 200005 | 3 |
| 200006 | 1 |
| ... | ... |
| 300001 | 3 |

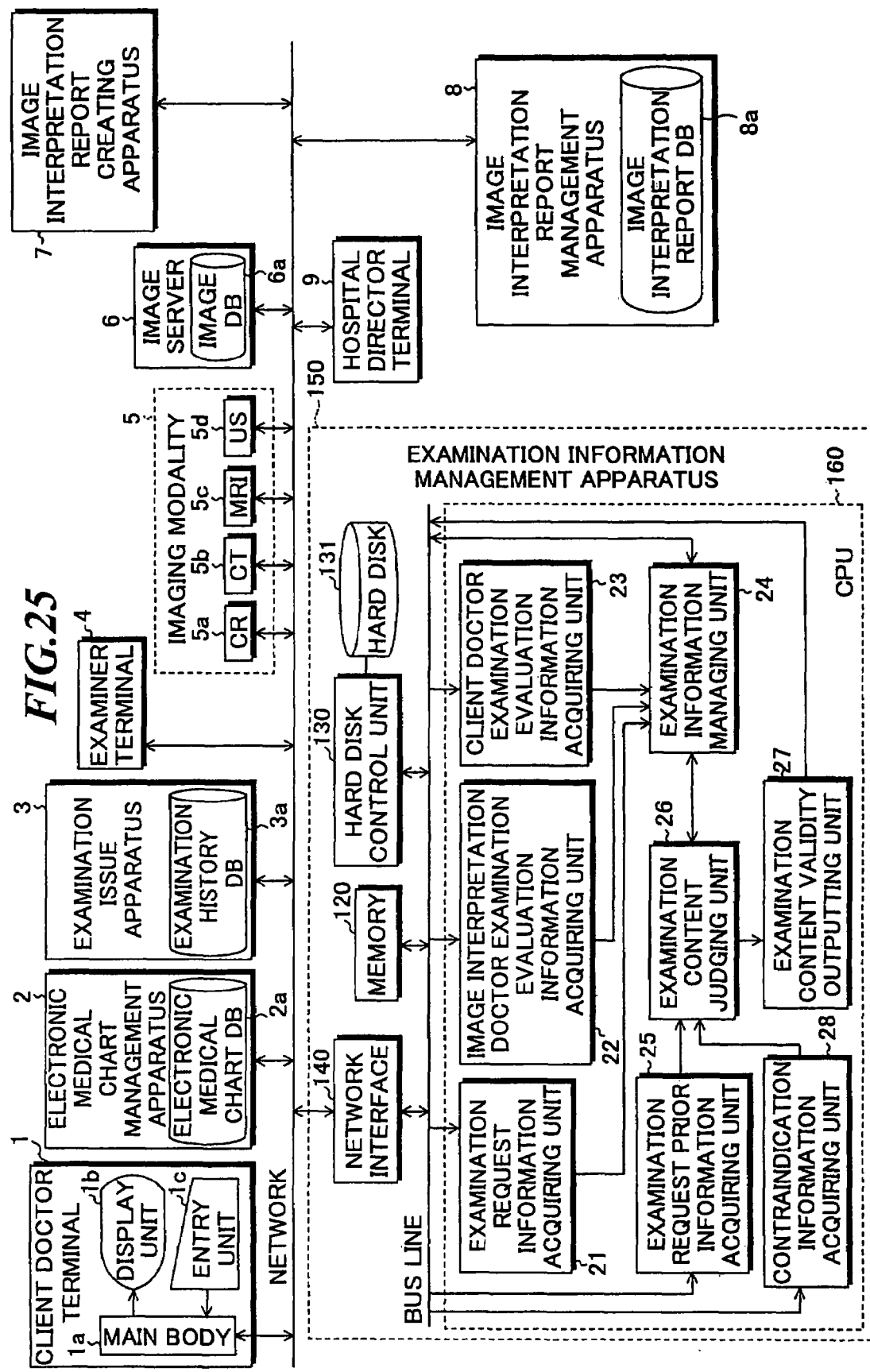

FIG.26

EXAMINATION HISTORY DB

| EXAMINATION ID | PATIENT ID | EXAMINATION TYPE | EXAMINATION CONTENT | PREDICTED DISEASE NAME | EXAMINATION DATE |
|---|---|---|---|---|---|
| US0001 | 000001 | US | ABDOMINAL US | FATTY LIVER | May 1, 2006 |
| US0002 | 000002 | US | ABDOMINAL US | FATTY LIVER | May 1, 2006 |
| CT0001 | 000003 | CT | ABDOMINAL CT | CIRRHOSIS | May 1, 2006 |
| CT0002 | 000004 | CT | ABDOMINAL CT | LIVER CANCER | May 1, 2006 |
| ZCT001 | 000005 | CONTRAST CT | ABDOMINAL CT CONTRAST | CIRRHOSIS | May 2, 2006 |
| US0003 | 000007 | US | ABDOMINAL US | CIRRHOSIS | May 2, 2006 |
| CT0004 | 000008 | CT | ABDOMINAL CT | FATTY LIVER | May 2, 2006 |
| MRI001 | 000009 | MRI | ABDOMINAL MRI | FATTY LIVER | May 2, 2006 |
| ... | ... | ... | ... | ... | ... |

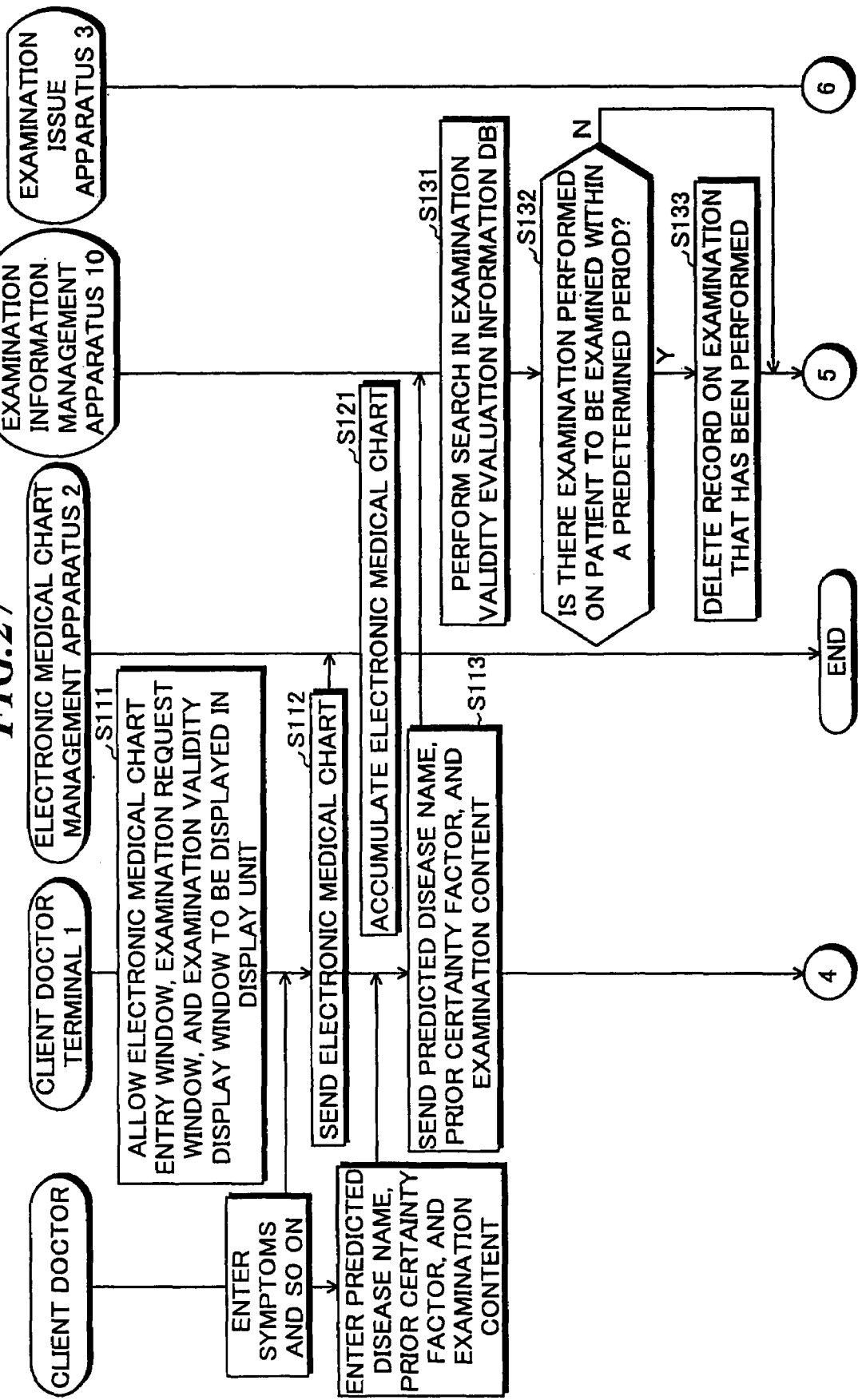

| PREVIOUS ILLNESSES, CAUSES, MAIN SYMPTOMS, AND SO ON | PRESCRIPTION, SURGERY, TREATMENT, AND SO ON |
|---|---|
| May 15, 2006, DOCTOR: Tanaka Ichiro<br>• MAJOR COMPLAINT<br>　LASSITUDE<br>　SWELLING<br>　JAUNDICE<br>• FINDING<br>　SUSPECTED TO HAVE<br>　FATTY LIVER<br>• CONTRAINDICATION<br>　DURING PREGNANCY,<br>　NO RADIOGRAPHIC EXAMINATION | |

( SAVE ELECTRONIC MEDICAL CHART ) — 51

43

EXAMINATION REQUEST

PREDICTED DISEASE NAME [　　　]

PRIOR CERTAINTY FACTOR [　　　]
　3　HIGHLY POSSIBLE
　2　POSSIBLE
　1　UNDENIABLE

EXAMINATION CONTENT [　　　]

( DISPLAY VALIDITY ) — 64

( REQUEST EXAMINATION ) — 65

44

EXAMINATION VALIDITY DISPLAY

FIG.32

| PREVIOUS ILLNESSES, CAUSES, MAIN SYMPTOMS, AND SO ON | PRESCRIPTION, SURGERY, TREATMENT, AND SO ON |
|---|---|
| May 15, 2006, DOCTOR: Tanaka Ichiro<br>• MAJOR COMPLAINT<br>  LASSITUDE<br>  SWELLING<br>  JAUNDICE<br>• FINDING<br>  SUSPECTED TO HAVE<br>  FATTY LIVER<br>• CONTRAINDICATION<br>  DURING PREGNANCY,<br>  NO RADIOGRAPHIC EXAMINATION | |

( SAVE ELECTRONIC MEDICAL CHART ) — 51

EXAMINATION REQUEST

PREDICTED DISEASE NAME: FATTY LIVER — 61

PRIOR CERTAINTY FACTOR: 3 — 62
  3  HIGHLY POSSIBLE
  2  POSSIBLE
  1  UNDENIABLE

EXAMINATION CONTENT: ABDOMINAL US — 63

( DISPLAY VALIDITY ) — 64
( REQUEST EXAMINATION ) — 65

EXAMINATION VALIDITY DISPLAY

• ABDOMINAL US WAS ALREADY PERFORMED ON PATIENT "Sato Hanako" ON May 1, 2006.
• PATIENT "Sato Hanako" IS IN PREGNANCY, NO RADIOGRAPHIC EXAMINATION IS ALLOWED FOR PATIENT "Sato Hanako"

| PREDICTED DISEASE NAME | PRIOR CERTAINTY FACTOR | EXAMINATION CONTENT | PROPERNESS FACTOR OF REQUESTED CONTENT | CERTAINTY FACTOR OF IMAGE INTERPRETATION RESULT | EFFECTIVENESS FACTOR OF IMAGE INTERPRETATION RESULT |
|---|---|---|---|---|---|
| FATTY LIVER | 3 | ABDOMINAL MRI | 1.2 | 1.2 | 1.8 |

FIG.34

EXAMINATION HISTORY DB

| EXAMINATION ID | PATIENT ID | EXAMINATION TYPE | EXAMINATION CONTENT | PREDICTED DISEASE NAME | EXAMINATION DATE |
|---|---|---|---|---|---|
| US0001 | 000001 | US | ABDOMINAL US | FATTY LIVER | May 1, 2006 |
| US0002 | 000002 | US | ABDOMINAL US | FATTY LIVER | May 1, 2006 |
| CT0001 | 000003 | CT | ABDOMINAL CT | CIRRHOSIS | May 1, 2006 |
| CT0002 | 000004 | CT | ABDOMINAL CT | LIVER CANCER | May 1, 2006 |
| CT0003 | 000005 | CT | ABDOMINAL CT | CIRRHOSIS | May 2, 2006 |
| ZCT001 | 000006 | CONTRAST CT | ABDOMINAL CT CONTRAST | CIRRHOSIS | May 2, 2006 |
| US0003 | 000007 | US | ABDOMINAL US | CIRRHOSIS | May 2, 2006 |
| CT0004 | 000008 | CT | ABDOMINAL CT | FATTY LIVER | May 2, 2006 |
| MRI001 | 000009 | MRI | ABDOMINAL MRI | FATTY LIVER | May 2, 2006 |
| ... | ... | ... | ... | ... | ... |
| MRI002 | 000002 | MRI | ABDOMINAL MRI | FATTY LIVER | May 15, 2006 |

EXAMINATION INFORMATION MANAGEMENT APPARATUS

BACKGROUND OF THE INVENTION

1. Field of the Invention

The present invention relates to an examination information management apparatus for supporting doctors to determine examination contents to be performed on patients.

2. Description of a Related Art

Recent years, various medical imaging apparatuses for CR (computed radiography), MRI (magnetic resonance imaging), CT (computed tomography), and US (ultrasonic imaging) have been widespread and used.

Generally, when an examination using a medical imaging apparatus is performed, image interpretation is performed on imaged medical images by an image interpretation doctor and an image interpretation report containing an interpretation result and findings is created before a specific diagnosis is made by a doctor in charge who requests the examination (also referred to as "client doctor"). Conventionally, even if digital image data is generated, medical images printed on photographic films have been used at the time of image interpretation. On the other hand, medical images displayed on monitors have been also used for image interpretation with the development of high-definition image monitors (viewers).

Since many medical imaging apparatuses are available as described above and the range of choices of examinations becomes wider, selection of examinations becomes difficult for doctors. Thus, it would be convenient for doctors at the time of selection of examinations to refer to information as guidelines for selection of examinations based on past examination records.

Japanese Patent Application Publication JP-P2003-281273A discloses a clinical examination system including a symptom entry unit to be used for entering symptoms of patients, a storage unit for storing relationships between symptoms and examination items, and an examination item candidate display unit for displaying examination item candidates selected from symptom information entered in the symptom entry unit based on the relationships between symptoms and examination items stored in the storage unit, and characterized in that the respective examination items are related to symptoms with necessity and stored with respect to the relationships between symptoms and examination items stored in the storage unit.

According to the clinical examination system, examination items can be automatically extracted based on symptoms of patients. However, the results of examinations that have been actually performed by using the clinical examination system can not be reflected in the relationships between symptoms and examination items stored in the storage unit, and therefore, experiences of separate client doctors and image interpretation doctors can not be accumulated. Further, it is conceivable that, some time during the use of the clinical examination system, the existence of an ineffective or improper relationship is found among the relationships between symptoms and examination items stored in the storage unit. In such a case, it is troublesome for an operator to surely delete the ineffective or improper relationship from the storage unit.

Further, Japanese Patent Application Publication JP-A-5-282384 discloses an examination item entry apparatus including storage means that have stored necessary combinations of plural examination items for each symptom, display means for displaying plural symptom names, and selecting means for selecting one of the displayed plural symptom names, and characterized in that plural examination items to be performed for the selected symptoms are loaded from the storage means and displayed on the display means in response to the selection.

According to the examination item entry apparatus, proper examination items for symptoms and disorders of patients can be easily entered. However, the results of examinations that have been actually performed by using the examination item entry apparatus can not be reflected in the necessary combinations of plural examination items for each symptom stored in the storage means, and therefore, experiences and knowledge obtained with respect to facilities in use of separate client doctors and image interpretation doctors can not be accumulated.

SUMMARY OF THE INVENTION

Accordingly, in view of the above-mentioned points, a purpose of the present invention is to provide an examination information management apparatus that enables more proper selection of examinations by accumulating experiences of individual client doctors and/or image interpretation doctors actually engaged in medical fields.

In order to achieve the purpose, an examination information management apparatus according to one aspect of the present invention is an examination information management apparatus connected directly or via a network to at least one image interpretation report creating apparatus to be used when an image interpretation doctor creates an image interpretation report based on medical images obtained with respect to an examination requested by a client doctor, for managing information on the examination to support selection of examination by the client doctor, and the apparatus includes: storage means for storing an examination evaluation database that accumulates information on evaluations of plural examinations performed for plural predicted disease names in the past; examination information managing means for managing the examination evaluation database; examination request prior information acquiring means for acquiring examination request prior information including information representing a disease name predicted by the client doctor and an examination candidate, and causing the examination information managing means to perform search in the examination evaluation database based on the examination request prior information; examination content judging means for acquiring information on an evaluation of the examination candidate for the disease name predicted by the client doctor based on the search performed by the examination managing means; and examination content validity outputting means for outputting the information on the evaluation acquired by the examination content judging means to a client doctor terminal to cause the client doctor terminal to display the evaluation of the examination candidate for the predicted disease name.

According to the present invention, information in which the evaluations of the examinations actually performed in the past are reflected is displayed on the client doctor terminal as a guideline for the client doctor to determine which examination is to be performed on a patient. Therefore, the client doctor can select a more proper examination.

BRIEF DESCRIPTION OF THE DRAWINGS

FIG. 1 is a block diagram showing a configuration of a medical information management system including an examination information management apparatus according to the first embodiment of the present invention;

FIGS. 2-5 show examples of a database stored in a hard disk shown in FIG. 1;

FIGS. 6 and 7 are the first half and the second half of a flowchart showing an operation of the medical information management system shown in FIG. 1;

FIG. 8 shows an electronic medical chart displayed on a display screen of a display unit of a client doctor terminal;

FIG. 9 is an enlarged view showing the first part of the electronic medical chart shown in FIG. 8;

FIGS. 10-13 are enlarged views showing the second part, an examination request window, and an examination validity display window of the electronic medical chart shown in FIG. 8;

FIG. 14 shows an example of a database stored in a hard disk shown in FIG. 1;

FIG. 19 shows an example of a database stored in a hard disk shown in FIG. 1;

FIGS. 21-23 show display screens of the display unit of the image interpretation doctor terminal in FIG. 1;

FIG. 24 shows an example of a database stored in a hard disk shown in FIG. 1;

FIG. 25 is a block diagram showing a configuration of a medical information management system including an examination information management apparatus according to the second embodiment of the present invention;

FIG. 26 shows an example of an examination history database in FIG. 25;

FIGS. 27-29 are three parts of a flowchart showing an operation of the medical information management system shown in FIG. 25;

FIG. 30-32 are enlarged views showing the second part, an examination request window, and an examination validity display window of an electronic medical chart displayed on a display unit of a client doctor terminal in FIG. 25;

FIG. 34 shows an example of an examination history database in FIG. 25.

DESCRIPTION OF THE PREFERRED EMBODIMENTS

Figure 7:
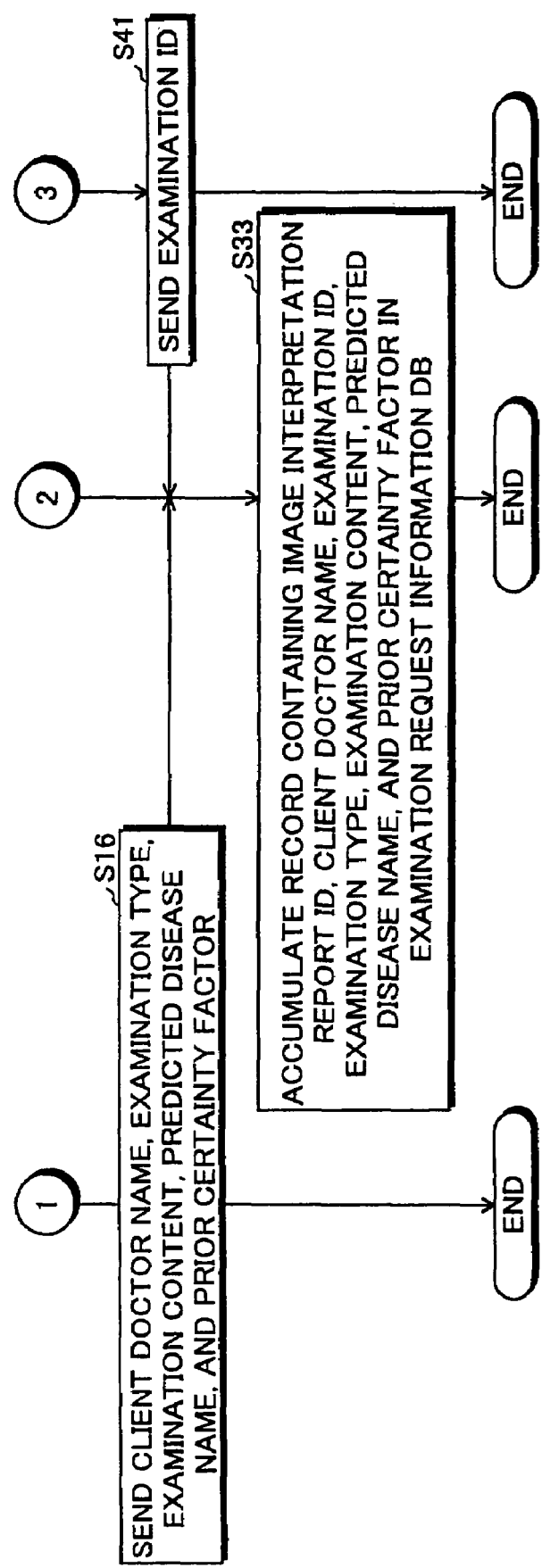

Hereinafter, preferred embodiments of the present invention will be explained in detail by referring to the drawings. The same reference numerals are assigned to the same component elements and the explanation thereof will be omitted.

FIG. 1 is a block diagram showing a configuration of a medical information management system including an examination information management apparatus according to the first embodiment of the present invention.

As shown in FIG. 1, the examination information management system includes a client doctor terminal 1, an electronic medical chart management apparatus 2, an examination issue apparatus 3, an examiner terminal 4, an imaging modality 5, an image server 6, an image interpretation report creating apparatus 7, an image interpretation report management apparatus 8, a hospital director terminal 9, and an examination information management apparatus 10 according to the first embodiment of the present invention. The imaging modality 5 includes a CR (computed radiography) apparatus 5a, a CT (computed tomography) apparatus 5b, an MRI (magnetic resonance imaging) apparatus 5c, and a US (ultrasonic imaging) apparatus 5d. These apparatuses may be connected to one another via a network such as LAN (local area network). Alternatively, the examination information management apparatus 10 may be directly connected to the client doctor terminal 1, the electronic medical chart management apparatus 2, the examination issue apparatus 3, the examiner terminal 4, the imaging modality 5, the image server 6, the image interpretation report creating apparatus 7, or the image interpretation report management apparatus 8.

The client doctor terminal 1 is a PC (personal computer) or the like to be used by a client doctor (e.g., a physician or the like) who requests an examination, and includes a main body 1a, a display unit 1b, and an entry unit 1c. The client doctor operates the client doctor terminal 1 to request examinations, view image interpretation reports, enter data into electronic medical charts, and so on. The client doctor terminal 1 may further include a high-definition display (viewer) for displaying medical images in addition to the main body 1a, the display unit 1b, and the entry unit 1c.

The electronic medical chart management apparatus 2 includes a recording medium for storing an electronic medical chart database (DB) 2a. The electronic medical chart database 2a accumulates electronic medical chart data of plural cases. The electronic medical chart contains information on public expenditure number, recipient number of public expenditure medical care, insurer number, patient name, diagnosis, treatment, and so on. The information of the electronic medical charts is entered by the client doctor in the client doctor terminal 1 and accumulated in the electronic medical chart database 2a.

The examination issue apparatus 3 is an apparatus for management of examinations, and manages examination schedules, makes orders for the imaging modality 5, and makes orders for image interpretation (image interpretation requests) on the examinations for which imaging has been completed, based on the inputted patient information and information of examination contents, and so on.

The examiner terminal 4 is a PC or the like to be used by an examiner (e.g., an examination doctor, imaging technician, or the like) who performs imaging of medical images. The examiner operates the examiner terminal 4 to know that requests of examinations have been made. When receiving a request of examination, the examiner uses a modality according to the examination content among the imaging modality 5 to perform imaging of medical images. The image data acquired by the imaging modality 5 is sent to the image server 6.

The image server 6 is a server for PACS (Picture Archiving and Communication System) for storage and management of the image data acquired by the imaging modality 5. The image server 6 outputs desired image data to the image interpretation report management apparatus 8 according to the request by the image interpretation report management apparatus 8.

The image interpretation report creating apparatus 7 is a PC or the like to be used by an image interpretation doctor who performs image interpretation based on the image data acquired by the imaging modality 5. The image interpretation report creating apparatus 7 includes a high-definition display (viewer) for display of medical images.

The image interpretation report management apparatus 8 includes a recording medium for storage of image interpretation report database 8a. The image interpretation report database 8a accumulates image interpretation report data representing the image interpretation reports that have been created in the past. The image interpretation report data contains image interpretation report ID, patient ID, patient name, examination ID, text information to be displayed as findings by the image interpretation doctor (finding data), and so on. The image interpretation report is entered by the image interpretation doctor in the image interpretation report creating apparatus 7 and accumulated in the image interpretation report database 8a. Further, the image interpretation report management apparatus 8 outputs desired image interpretation report data to the client doctor terminal 1 according to the request by the client doctor terminal 1.

The hospital director terminal 9 is a PC or the like to be used by a hospital director.

The examination information management apparatus 10 includes a central processing unit (hereinafter, referred to as CPU) 20, a memory 120 for temporary storage of various data and so on, a hard disk control unit 130 for control of a hard disk 131 as a recording medium, and a network interface 140. These are interconnected via a bus line. Further, the CPU 20 is connected to the network via the network interface 140. In the embodiment, the examination information management apparatus 10 is an independent apparatus, however, the examination information management apparatus 10 may be realized as a part of the client doctor terminal 1 or the image interpretation report management apparatus 8.

In the hard disk 131, not only the software (programs) for actuating the CPU 20 to perform processing, but also an examination request information database for accumulating examination request information containing examination content, predicted disease name, prior certainty factor, and so on entered by the client doctor before the request of an examination into the client doctor terminal 1, an image interpretation doctor examination evaluation information database for accumulating image interpretation doctor examination evaluation information entered by the image interpretation doctor at the time of image interpretation into the image interpretation report creating apparatus 7, and a client doctor examination evaluation information database for accumulating client doctor examination evaluation information entered by the client doctor when the doctor makes a diagnosis (decides a disease name) into the client doctor terminal 1 are recorded. Furthermore, in the hard disk 131, an examination validity evaluation information database generated based on the examination request information database, the image interpretation doctor examination evaluation information database, and the client doctor examination evaluation information database is also recorded. In this application, these databases are collectively referred to as "examination evaluation database".

As the recording medium, not only the built-in hard disk 131, but also an external hard disk, flexible disk, MO, MT, RAM, CD-ROM, DVD-ROM, or the like may be used.

FIG. 2 shows an example of the examination request information database. As shown in FIG. 2, the examination request information contains an image interpretation report ID for uniquely identifying an image interpretation report, client doctor name, examination ID for uniquely identifying an examination, examination type, predicted disease name, prior certainty factor, and examination content. Here, the prior certainty factor will be explained. At the time of consultation of a patient, the client doctor enters a major complaint and symptoms of the patient into an electronic medical chart by using the client doctor terminal 1, and enters the predicted disease name and examination content considered to be proper for making a diagnosis (deciding a disease name) in the client doctor terminal 1. Furthermore, the client doctor enters the prior certainty factor representing the degree of certainty that the predicted disease name is correct (the predicted disease name and the disease name to be decided will be the same) in the client doctor terminal 1. In the embodiment, the client doctor enters "3" as the prior certainty factor when the doctor considers that there is a high possibility that the predicted disease name is correct, enters "2" as the prior certainty factor when the doctor considers that there is a possibility that the predicted disease name is correct, and enters "1" as the prior certainty factor when the doctor considers that the possibility that the predicted disease name is correct is not deniable. Thus, the predicted disease name, examination content, prior certainty factor entered in the client doctor terminal 1 are sent from the client doctor terminal 1 to the examination information management apparatus 10 and accumulated in the examination request information database. The examination ID is determined by the examination issue apparatus 3, and the image interpretation report ID is determined by the image interpretation report management apparatus 8.

FIG. 3 shows an example of an image interpretation doctor examination evaluation information database. As shown in FIG. 3, the image interpretation doctor examination evaluation information contains the image interpretation report ID, finding, image interpretation doctor diagnostic result (disease name decided by the image interpretation doctor), image interpretation doctor name, properness factor of requested content, and certainty factor of image interpretation result.

Here, the properness factor of requested content and certainty factor of image interpretation result would be explained. After imaging of medical images is performed in the imaging modality 5 according to an examination request by the client doctor, the image interpretation doctor creates an image interpretation report based on the medical images displayed on the viewer in the image interpretation report creating apparatus 7. Furthermore, when creating the image interpretation report, the image interpretation doctor enters the properness factor of requested content representing the degree whether the examination content requested by the client doctor is proper for decision of image interpretation doctor diagnostic result (disease name) is proper or not with the certainty factor of image interpretation result representing the degree of certainty that the image interpretation result is correct (the image interpretation doctor diagnostic result will be coincident with the disease name to be decided) as values "1" to "3" in the image interpretation report creating apparatus 7.

In the embodiment, the client doctor enters "3" as the properness factor of requested content when the doctor judges that the examination content requested by the client doctor is proper, enters "2" as the properness factor of requested content when the doctor judges that the properness of the examination content requested by the client doctor is not deniable, and enters "1" as the properness factor of requested content when the doctor judges that the examination content requested by the client doctor is improper. Further, the client doctor enters "3" as the certainty factor of image interpretation result when the degree that the doctor feels certain that the image interpretation result is correct is high, enters "2" as certainty factor of image interpretation result when the doctor judges that there is a possibility that the image interpretation result is correct, and enters "1" as the certainty factor of image interpretation result when the degree that the doctor feels certain that the image interpretation result is correct is low.

Thus entered properness factor of requested content and certainty factor of image interpretation result in the image interpretation report creating apparatus 7 are sent from the image interpretation report creating apparatus 7 to the examination information management apparatus 10 via the network and accumulated in the image interpretation doctor examination evaluation information database.

FIG. 4 shows an example of the client doctor examination evaluation information database. As shown in FIG. 4, the client doctor examination evaluation information contains the image interpretation report ID and effectiveness factor of image interpretation result. When an image interpretation report is created by the image interpretation doctor, the client doctor makes a diagnosis (decides a disease name) while referring to the image interpretation report by using the client doctor terminal 1. Furthermore, the client doctor enters the effectiveness factor of image interpretation result representing the degree that the image interpretation report is effective for making the diagnosis as values "1" to "3" in the client doctor terminal 1.

In the embodiment, the client doctor enters "3" as the effectiveness factor of image interpretation result when the doctor judges that the image interpretation report is very effective for making the diagnosis, enters "2" as the effectiveness factor of image interpretation result when the doctor judges that the image interpretation report is effective for making the diagnosis, and enters "1" as the effectiveness factor of image interpretation result when the doctor judges that the image interpretation report is ineffective for making the diagnosis. Thus entered effectiveness factor of image interpretation result in the client doctor terminal 1 is sent from the client doctor terminal 1 to the examination information management apparatus 10 and accumulated in the client doctor examination evaluation information database.

FIG. 5 shows an example of the examination validity evaluation information database. As shown in FIG. 5, the examination validity evaluation information database contains the predicted disease name, prior certainty factor, examination content, average value of properness factors of requested content on plural examinations performed in the past with respect to them, average value of certainty factors of image interpretation result on the examinations, and average value of effectiveness factors of image interpretation result on the examinations.

That is, under a condition of a set of predicted disease name, prior certainty factor, and examination content, the average value of properness factors of requested content on plural examinations that match the condition and the average value of certainty factors of image interpretation result on the plural examinations that match the condition can be obtained in the following manner, for example. First, search is performed in the examination request information database by using a set of predicted disease name, prior certainty factor, and examination content as a search key, and plural records are extracted. Then, search is performed in the image interpretation doctor examination evaluation information database by using plural image interpretation report IDs contained in the extracted plural records as search keys, and plural records are extracted. Then, the average value of plural properness factors of requested content and the average value of plural certainty factors of image interpretation result contained in the extracted plural records are respectively calculated. In this manner, under a condition of a set of predicted disease name, prior certainty factor, and examination content, the average value of properness factors of requested content on plural examinations that match the condition and the average value of certainty factors of image interpretation result on the plural examinations that match the condition can be obtained.

Further, under a condition of a set of predicted disease name, prior certainty factor, and examination content, the average value of effectiveness factors of image interpretation result on the plural examinations that match the condition can be obtained in the following manner, for example. First, search is performed in the examination request information database by using a set of predicted disease name, prior certainty factor, and examination content as a search key, and plural records are extracted. Then, search is performed in the client doctor examination evaluation information database by using plural image interpretation report IDs contained in the extracted plural records as search keys, and plural records are extracted. Then, the average value of plural effectiveness factors of image interpretation result contained in the extracted plural records is calculated. In this manner, under a condition of a set of predicted disease name, prior certainty factor, and examination content, the average value of effectiveness factors of image interpretation result on the plural examinations that match the condition can be obtained.

Alternatively, under a condition of a set of predicted disease name, prior certainty factor, and examination content, the average value of properness factors of requested content on plural examinations that match the condition, the average value of certainty factors of image interpretation result on the plural examinations that match the condition, and the average value of effectiveness factors of image interpretation result that match the condition can be obtained in the following manner, for example. First, the examination request information database, the image interpretation doctor examination evaluation information database, and the client doctor examination evaluation information database are joined by using an image interpretation report ID as a search key. Then, search is performed in the database resulting from joining them by using a set of predicted disease name, prior certainty factor, and examination content as a search key, and plural records are extracted. Then, the average value of plural properness factors of requested content, the average value of plural certainty factors of image interpretation result, and the average value of plural effectiveness factors of image interpretation result contained in the extracted plural records are calculated. In this manner, under a condition of a set of predicted disease name, prior certainty factor, and examination content, the average value of properness factors of requested content on plural examinations that match the condition, the average value of certainty factors of image interpretation result on the plural examinations that match the condition, and the average value of effectiveness factors of image interpretation result on the plural examinations that match the condition can be obtained.

Next, referring to FIG. 1, plural functional blocks configured by the CPU 20 and software (programs) will be explained. These functional blocks include an examination request information acquiring unit 21, an image interpretation doctor examination evaluation information acquiring unit 22, a client doctor examination evaluation information acquiring unit 23, an examination information managing unit 24, an examination request prior information acquiring unit 25, an examination content judging unit 26, and an examination content validity outputting unit 27.

The examination request information acquiring unit 21 receives from the client doctor terminal 1 the client doctor name, examination type, examination content, predicted disease name, prior certainty factor, and so on entered by the client doctor at the time of request of examination in the client doctor terminal 1 and outputs them to the examination information managing unit 24.

The image interpretation doctor examination evaluation information acquiring unit 22 receives from the image interpretation report creating apparatus 7 the finding, diagnosis, image interpretation doctor name, properness factor of requested content, certainty factor of image interpretation result, and so on entered by the image interpretation doctor at the creation of the image interpretation report in the image interpretation report creating apparatus 7 and outputs them to the examination information managing unit 24.

The client doctor examination evaluation information acquiring unit 23 receives from the client doctor terminal 1 the effectiveness factor of image interpretation result and so on entered by the client doctor at the time of reference to the image interpretation report in the client doctor terminal 1 and outputs them to the examination information managing unit 24.

The examination information managing unit 24 receives the client doctor name, examination type, examination content, predicted disease name, prior certainty factor, and so on from the examination request information acquiring unit 21, the examination ID from the examination issue apparatus 3, and the image interpretation report ID from the image interpretation report management apparatus 8, respectively, and accumulates them in the examination request information database. Further, the examination information managing unit 24 receives the finding, diagnosis, image interpretation doctor name, properness factor of requested content, and certainty factor of image interpretation result from the image interpretation doctor examination evaluation information acquiring unit 22, and accumulates them with the image interpretation report ID in the image interpretation doctor examination evaluation information database. Furthermore, the examination information managing unit 24 receives the effectiveness factor of image interpretation result from the client doctor terminal 1 and accumulates it with the image interpretation report ID in the client doctor examination evaluation information database. In addition, the examination information managing unit 24 creates or updates the examination validity evaluation information database based on the examination request information database, the image interpretation doctor examination evaluation information database, and the client doctor examination evaluation information database.

The examination request prior information acquiring unit 25 receives from the client doctor terminal 1 the predicted disease name, prior certainty factor, examination content, and so on entered by the client doctor before the request of an examination in the client doctor terminal 1, and outputs them to the examination content judging unit 26.

The examination content judging unit 26 receives the predicted disease name, prior certainty factor, examination content, and so on from the examination request prior information acquiring unit 25, and outputs the predicted disease name, or the predicted disease name and prior certainty factor to the examination information managing unit 24. When receiving the predicted disease name, or the predicted disease name and prior certainty factor from the examination content judging unit 26, the examination information managing unit 24 performs search in the examination validity evaluation information database by using the predicted disease name, or the predicted disease name and prior certainty factor as the search key, and outputs the records obtained as a search result to the examination content judging unit 26. The examination content judging unit 26 receives the records obtained as the search result from the examination information managing unit 24 and outputs them to the examination content validity outputting unit 27.

The examination content validity outputting unit 27 sends the records received from the examination content judging unit 26 to the client doctor terminal 1 and causes the client doctor terminal 1 to display them.

Next, an operation of the medical information management system will be explained. FIGS. 6 and 7 are flowcharts showing the operation of the medical information management system when the client doctor makes an examination request.

Figure 8:
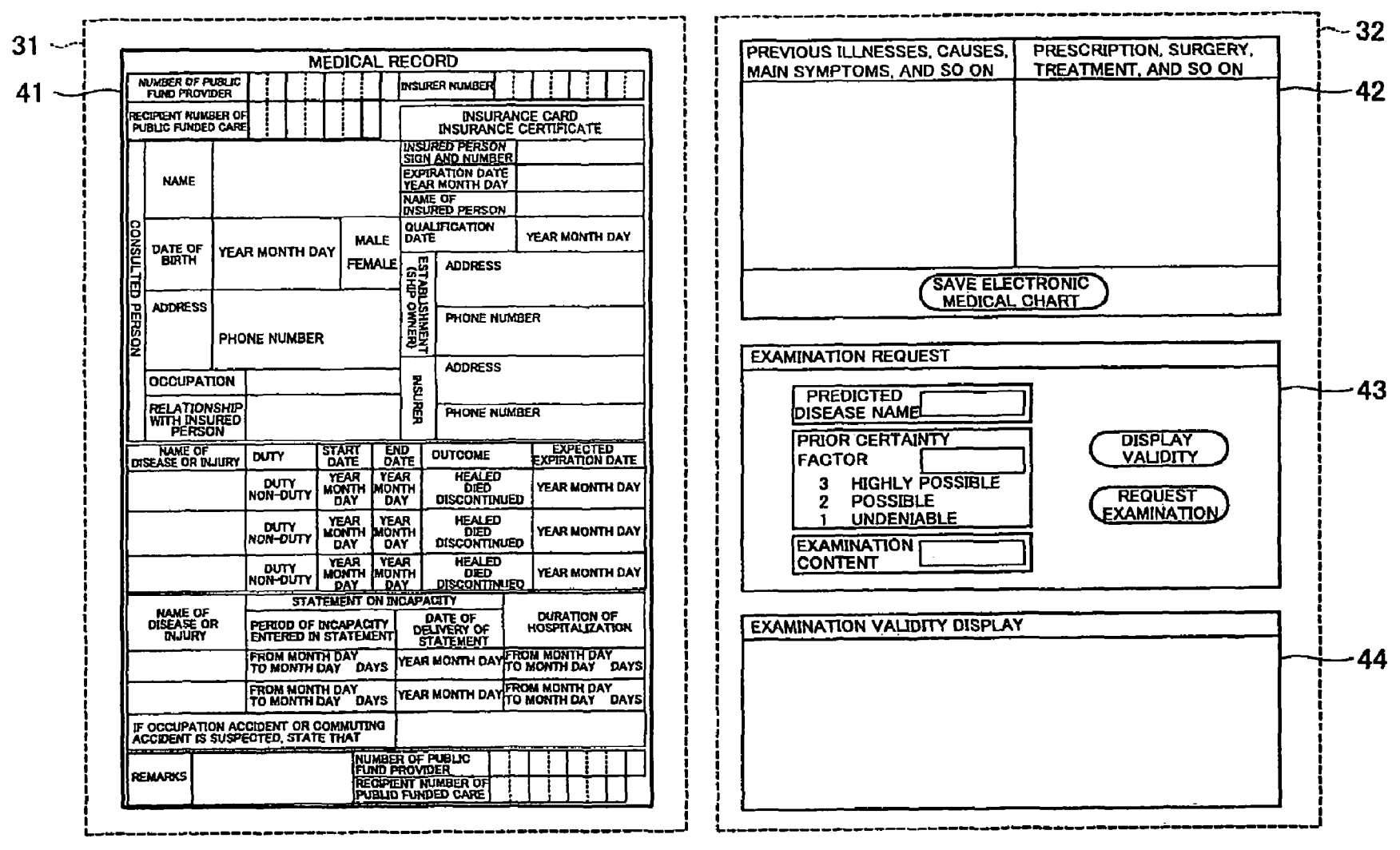

First, the client doctor terminal 1 allows an electronic medical chart entry window, an examination request window, and an examination validity display window to be displayed on the display unit 1b (step S11). FIG. 8 shows an example of display screen of the display unit 1b of the client doctor terminal 1. FIG. 9 is an enlarged view of an area 31 of FIG. 8, and FIG. 10 is an enlarged view of an area 32 of FIG. 8.

As shown in FIG. 9, the first part 41 of the electronic medical chart entry window is displayed within the area 31 of FIG. 8. In the electronic medical chart, number of public fund provider, recipient number of public funded care, insurer number, insured person sign and number, and soon are included as items required to be entered on insurance medical institution's responsibility, and name of disease or injury, start date, end date, outcome, and so on are included as items required to be entered on insurance doctor's responsibility. As a name of disease or injury, a disease name such as "fatty liver" or "cirrhosis" is entered. In addition to the information, patient name and so on are entered in the first part 41 of the electronic medical chart entry window. For example, the patient name is "Yamada Saburo", the patient ID is "000101", the patient sex is "male", and the patient age is "51".

As shown in FIG. 10, the second part 42 of the electronic medical chart entry window, the examination request window 43, and the examination validity display window are displayed within the area 32 of FIG. 8. The second part 42 of the electronic medical chart entry window contains an electronic medical chart save button 51. The client doctor enters patient symptoms and so on in the second part 42 of the electronic medical chart entry window. FIG. 11 shows the second part 42 of the electronic medical chart entry window in which the consultation date (here, "May 15, 2006"), client doctor name (here, "Tanaka Ichiro"), patient symptoms (here, "lassitude", "swelling", and "jaundice"), finding based on the patient symptoms (here, "suspected to have fatty liver") have been entered. After entering the patient symptoms and so on, the client doctor clicks the electronic medical chart save button 51 with a mouse.

When the electronic medical chart save button 51 is clicked, the client doctor terminal 1 sends the information of the electronic medical chart to the electronic medical chart management apparatus 2 (step S12), and the electronic medical chart management apparatus 2 accumulates the received information of the electronic medical chart in the electronic medical chart database 2a (step S21).

Then, the client doctor decides the predicted disease name based on the patient symptoms. Here, the client doctor decides the predicted disease name as "fatty liver" based on the patient symptoms of "lassitude", "swelling", and "jaundice". Further, here, the client doctor judges that there is a high possibility that the diagnostic result (decided disease name) will be "fatty liver", that is, the prior certainty factor is "3". Furthermore, the client doctor attempts to make an examination request of examination content "abdominal US" for diagnosis of "fatty liver". Then, the client doctor enters the predicted disease name "fatty liver" in a predicted disease name entry field 61 within the examination request window 43, the prior certainty factor "3" in a prior certainty factor entry field 62, and the examination content to request "abdominal US" in an examination content entry field 63, respectively. FIG. 12 shows the area 32 (FIG. 8) of the display screen of the display unit 1b of the client doctor terminal 1 in this case. Then, the client doctor clicks a validity display button 64 within the examination request window 43 with the mouse. When the validity display button 64 is clicked, the client doctor terminal 1 sends the predicted disease name, the prior certainty factor, and the examination content to the examination information management apparatus 10 (step S13).

When receiving the predicted disease name, the prior certainty factor, and the examination content from the client doctor terminal 1, the examination request prior information acquiring unit 25 of the examination information management apparatus 10 outputs the received predicted disease name, prior certainty factor, and examination content to the examination content judging unit 26. The examination content judging unit 26 outputs the predicted disease name, or the predicted disease name and prior certainty factor to the examination information managing unit 24. The examination information managing unit 24 performs search in the examination validity evaluation information database (see FIG. 5) by using the predicted disease name, or the predicted disease name and prior certainty factor received from the examination content judging unit 26 as search keys.

In the case where the predicted disease name and the prior certainty factor are used as search keys, the examination information managing unit 24 extracts the first to third records within the examination validity evaluation information database shown in FIG. 5 as search results because the predicted disease name is "fatty liver" and the prior certainty factor is "3". Then, the examination information managing unit 24 outputs the search results to the examination content judging unit 26. The examination content judging unit 26 outputs the examination content received from the examination request prior information acquiring unit 25 and the search results received from the examination information managing unit 24 to the examination content validity outputting unit 27. The examination content validity outputting unit 27 sends the search results (here, the first to third records within the examination validity evaluation information database shown in FIG. 5) to the client doctor terminal 1 and causes them to be displayed in the client doctor terminal 1 (step S32). In this regard, the examination content validity outputting unit 27 may cause the record (here, the first record within the examination validity evaluation information database shown in FIG. 5) that matches the examination content (here, "abdominal US") received from the examination request prior information acquiring unit 25 to be highlighted (e.g., shaded, bold or the like) in the client doctor terminal 1. Further, the examination content validity outputting unit 27 may cause a warning to be displayed in the client doctor terminal 1 when the properness factor of requested content, the certainty factor of image interpretation result, or the effectiveness factor of image interpretation result within the record that matches the examination content received from the examination request prior information acquiring unit 25 is a predetermined value (e.g., less than "2" or the like).

In the case where the predicted disease name is used as the search key, the examination content judging unit 26 outputs the examination content received from the examination request prior information acquiring unit 25 and at least the search results of the same examination content as the examination content received from the examination request prior information acquiring unit 25 to the examination content validity outputting unit 27. Furthermore, the examination content judging unit 26 may output a predetermined number of search results including search results in which at least one of the properness factor of requested content, the certainty factor of image interpretation result, or the effectiveness factor of image interpretation result is high to the examination content validity outputting unit 27. The examination content validity outputting unit 27 sends those search results to the client doctor terminal 1 and causes them to be displayed in the client doctor terminal 1 (step S32).

The client doctor terminal 1 receives the search results performed in the examination information management apparatus 10, and causes them to be displayed on the display unit 1b within the examination validity display window 44 (step S14). FIG. 13 shows the area 32 (FIG. 8) of the display screen of the display unit 1b of the client doctor terminal 1. As shown in FIG. 13, within the examination validity display window 44, under the condition of a set of the predicted disease name "fatty liver", the prior certainty factor "3", and the examination content "abdominal US", the average value "2.8" of properness factors of requested content, the average value "2.6" of certainty factors of image interpretation result, and the average value "2.9" of effectiveness factors of image interpretation result on plural examinations that match the condition (corresponding to the first record within the examination validity evaluation information database shown in FIG. 5) are highlighted (here, shaded). Further, within the examination validity display window 44, under the condition of a set of the predicted disease name "fatty liver", the prior certainty factor "3", and the examination content "abdominal CT", the average value "2.9" of properness factors of requested content, the average value "2.6" of certainty factors of image interpretation result, and the average value "2.8" of effectiveness factors of image interpretation result on plural examinations that match the condition (corresponding to the second record within the examination validity evaluation information database shown in FIG. 5) are also displayed. Furthermore, within the examination validity display window 44, under the condition of a set of the predicted disease name "fatty liver", the prior certainty factor "3", and the examination content "abdominal MRI", the average value "1.2" of properness factors of requested content, the average value "1.2" of certainty factors of image interpretation result, and the average value "1.8" of effectiveness factors of image interpretation result on plural examinations that match the condition (corresponding to the third record within the examination validity evaluation information database shown in FIG. 5) are also displayed.

Referring to the examination validity display window 44 shown in FIG. 13, the client doctor may found that the examination of examination content "abdominal US" or "abdominal CT" is more proper than the examination of examination content "abdominal MRI" in the case where the predicted disease name is "fatty liver" and the prior certainty factor is "3". Then, the client doctor judges whether or not the client doctor makes a request for the examination of the examination content entered in the examination content entry field 63 of the examination request window 43 (here, "abdominal US").

In the case where the client doctor judges to make a request not for the examination of the examination content entered in the examination content entry field 63 of the examination request window 43, but for the examination of the other examination content (e.g., "abdominal CT"), the doctor may enter the examination content in the examination content entry field 63 of the examination request window 43. In this regard, the client doctor may click the validity display button 64 again. In response, the client doctor terminal 1 executes steps S13 and S14 again, and the examination information management apparatus 10 executes steps S31 and S32 again.

On the other hand, in the case where the client doctor judges to make a request for the examination of the examination content entered in the examination content entry field 63 of the examination request window 43 (here, "abdominal US"), the doctor clicks an examination request button 65 within the examination request window 43.

When the examination request button 65 is clicked, the client doctor terminal 1 sends the patient name (here, "Yamada Saburo"), patient ID (here, "000101"), examination type (here, "US"), examination content (here, "abdominal US"), and predicted disease name (here, "fatty liver") to the examination issue apparatus 3 (step S15), and sends the client doctor name (here, "Tanaka Ichiro"), the examination type, the examination content, the predicted disease name, and the prior certainty factor (here, "3") to the examination information management apparatus 10 (step S16).

When receiving the patient name, the patient ID, the examination type, the examination content, and the predicted disease name from the client doctor terminal 1, the examination issue apparatus 3 determines the examination ID (here, "US1001") and sends the determined examination ID to the examination information management apparatus 10 (step S41). The examination issue apparatus 3 causes the determined examination ID, the patient name, the patient ID, the examination type, the examination content, and the predicted disease name to be displayed in the examiner terminal 4. The examiner refers to the patient name and so on displayed in the display unit of the examiner terminal 4 and performs the examination by using the imaging modality 5. The medical image data obtained in the imaging modality 5 is sent to the image server 6 and accumulated in the image database 6*a*. Further, the image interpretation report ID (here, "300001") is determined in the image interpretation report management apparatus 8 and sent to the examination information management apparatus 10.

The examination request information acquiring unit 21 of the examination information management apparatus 10 receives the client doctor name, the examination type, the examination content, the predicted disease name, and the prior certainty factor from the client doctor terminal 1, the examination ID from the examination issue apparatus 3, and the image interpretation report ID from the image interpretation report management apparatus 8, respectively, and outputs the information to the examination information managing unit 24. The examination information managing unit 24 accumulates the record including the image interpretation report ID (here, "300001"), the client doctor name (here, "Tanaka Ichiro"), the examination type (here, "US"), the examination content (here, "abdominal US"), the predicted disease name (here, "fatty liver"), and the prior certainty factor (here, "3") in the examination request information database (step S33). FIG. 14 shows the examination request information database in this case. As shown in FIG. 14, a new record including the above-mentioned information is added to the lowermost row of the examination request information database.

Figure 15:
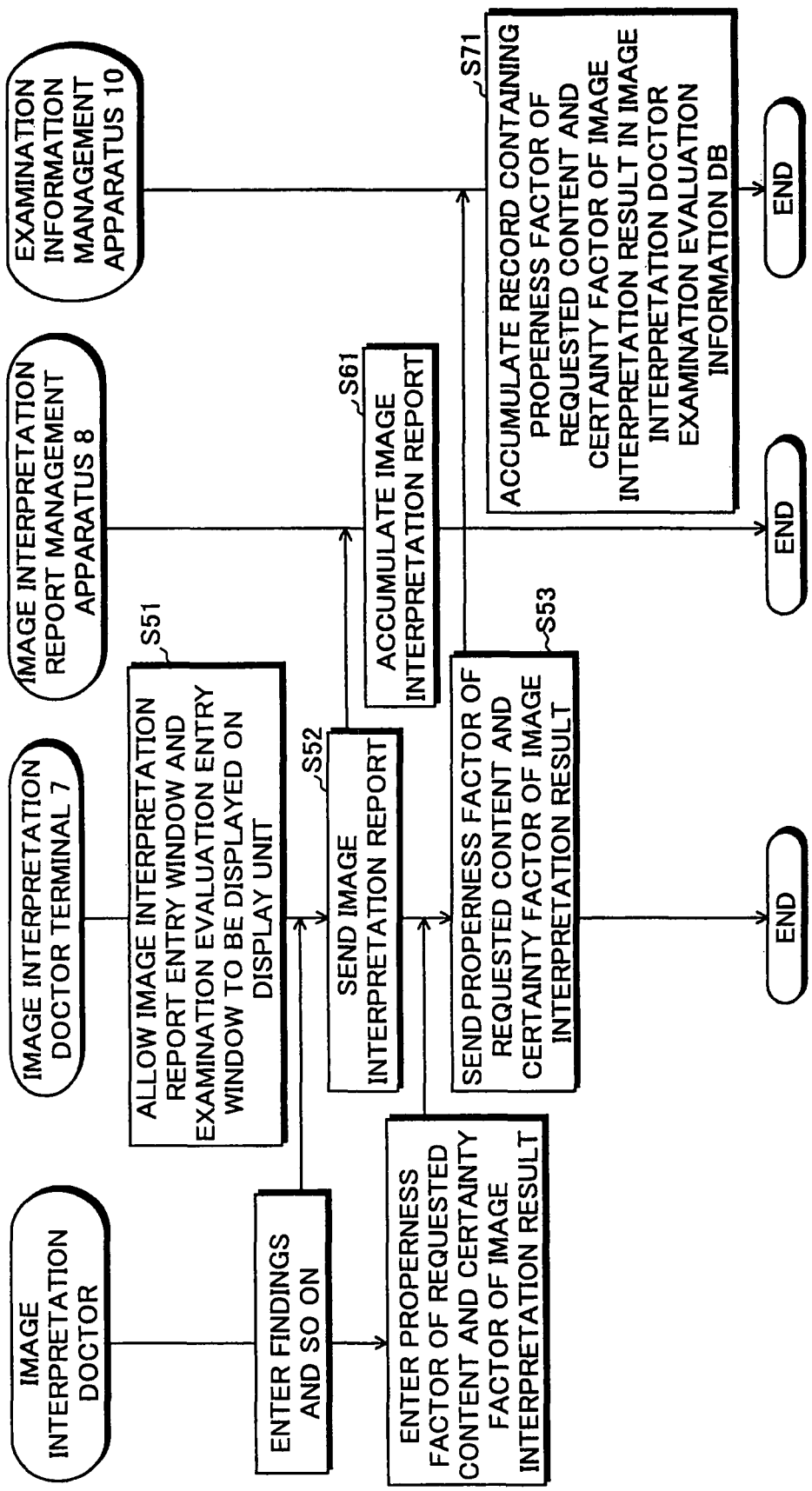
FIG. 15 is a flowchart showing an operation of the medical information management system shown in FIG. 1.

Next, an operation of the medical information management system when the image interpretation doctor performs image interpretation will be explained with reference to FIG. 15. FIG. 15 is a flowchart showing the operation of the medical information management system when the image interpretation doctor performs image interpretation.

Figure 16:
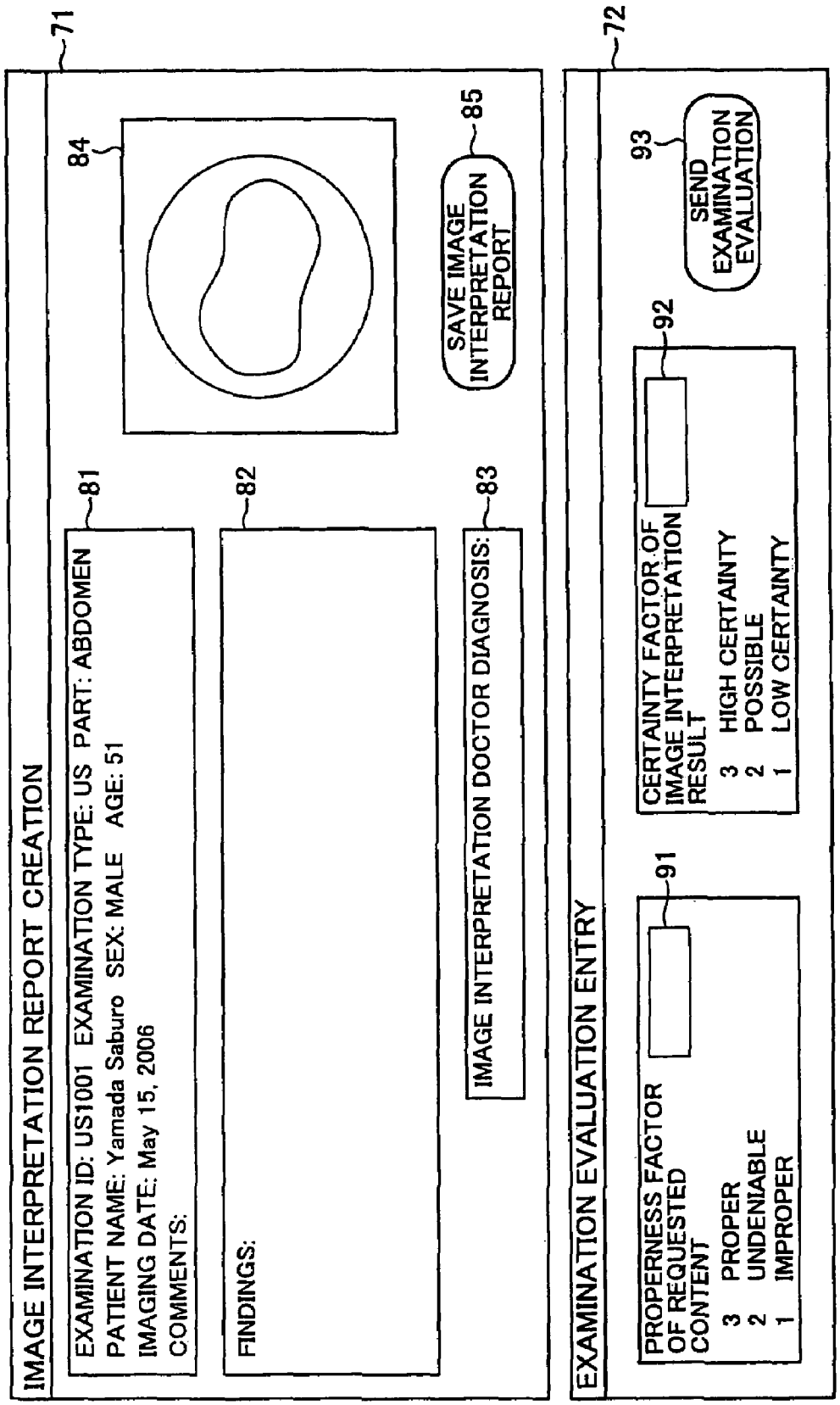
FIGS. 16-18 show image interpretation report creation windows displayed on a display unit of an image interpretation doctor terminal in FIG. 1.

First, the image interpretation report creating apparatus 7 causes an image interpretation report entry window and an examination evaluation entry window to be displayed on the display unit (step S51). FIG. 16 shows an example of display screen of the display unit of the image interpretation report creating apparatus 7. As shown in FIG. 16, the image interpretation report entry window 71 and the examination evaluation entry window 72 are displayed in the display unit of the image interpretation report creating apparatus 7. The image interpretation report entry window 71 contains an examination information display field 81, a finding entry field 82, an diagnosis by the diagnosis entry field 83, a key image display field 84, and an image interpretation report save button 85, and the examination evaluation entry window 72 contains a requested content properness factor entry field 91, an image interpretation result certainty factor entry field 92, and an examination evaluation send button 93.

In the examination information display field 81, the examination ID (here, "US1001"), examination type (here, "US"), a part to be examined (here, "abdomen"), patient name (here, "Yamada Saburo"), sex (here, "male"), age (here, "51"), imaging date (here, "May 15, 2006), and comments on the examination are displayed. In the key image display field 84, an image judged by the image interpretation doctor to be a key for image interpretation in a series of images obtained by the examination (key image) is displayed. The image interpretation report creating apparatus 7 has a high-definition image monitor (viewer) and the series of images obtained by the examination are displayed on the viewer.

Figure 17:
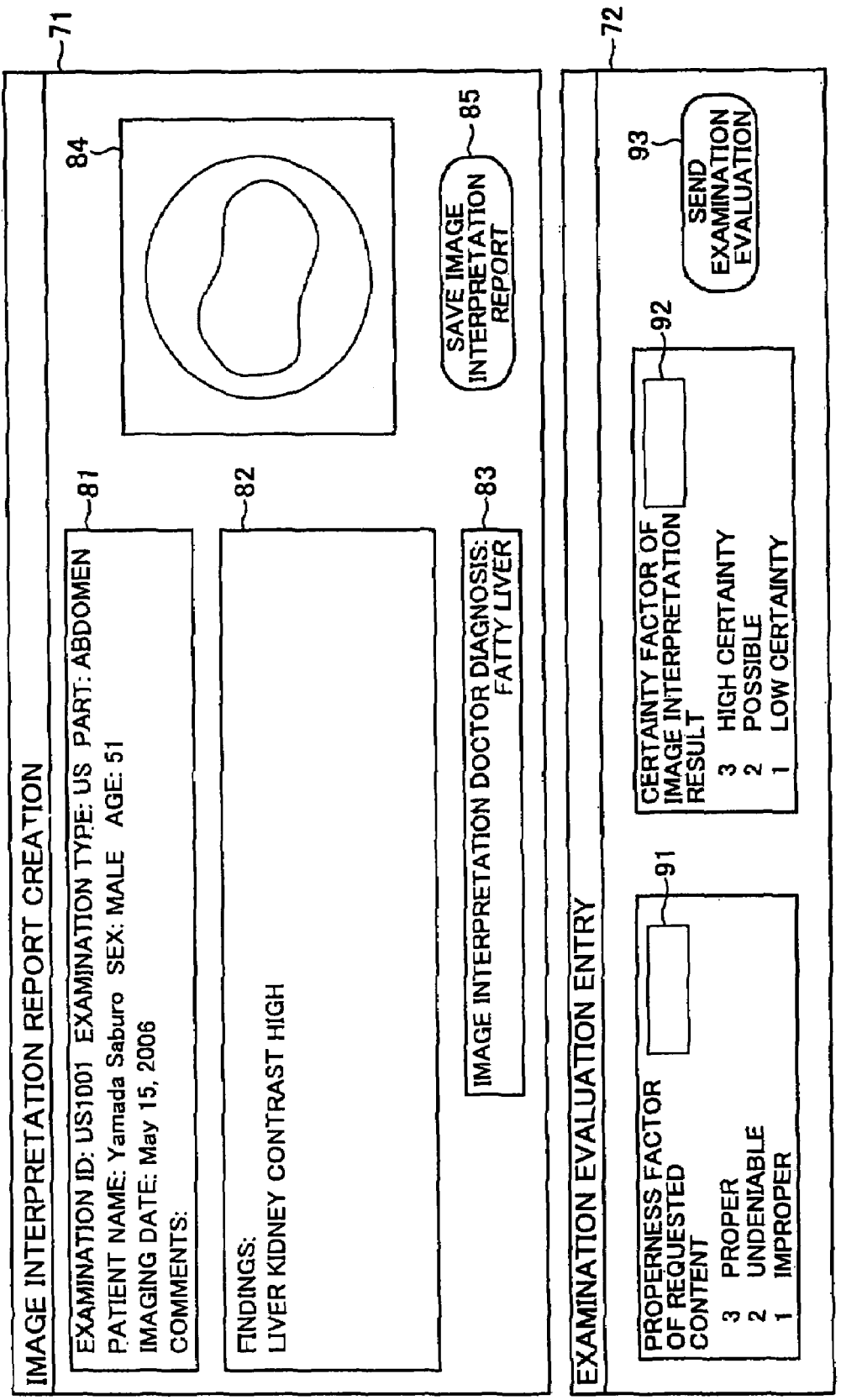

The image interpretation doctor (here, "Fuji Taro") enters a finding (here, "liver kidney contrast high") into the finding entry field 82, and image interpretation doctor diagnostic result (here, "fatty liver") into the diagnosis entry field 83, while watching the key image display field 84 or an image displayed on the viewer. FIG. 17 shows the finding entry field 82 and the diagnosis entry field 83 in which the finding and the image interpretation diagnosis have been entered, respectively. After entering finding and the image interpretation diagnosis, the image interpretation doctor clicks the image interpretation report save button 85.

When the image interpretation report save button 85 is clicked, the image interpretation report creating apparatus 7 sends the image interpretation report to the image interpretation report management apparatus 8 (step S52), and the image interpretation report management apparatus 8 accumulates the image interpretation report in the image interpretation report database 8*a* (step S53).

Figure 18:
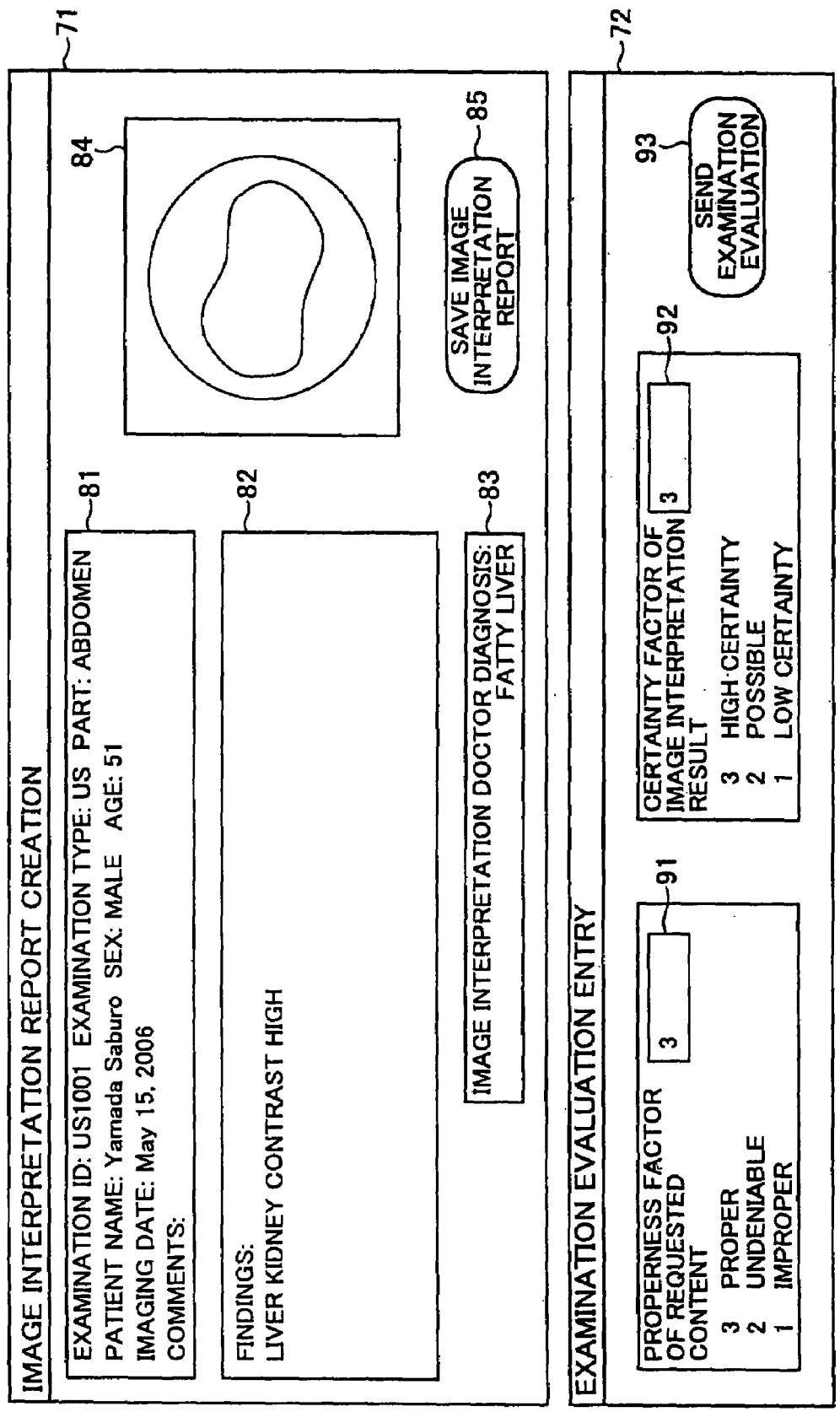

Then, the image interpretation doctor enters the properness factor of requested content (here, "3") representing the degree whether the examination content "abdominal US" requested by the client doctor is proper for diagnosis as "fatty liver" into the requested content properness factor entry field 91. Furthermore, the image interpretation doctor enters the certainty factor of image interpretation result (here, "3") as the degree that the image interpretation result is correct, that is, the doctor feels certain that the image interpretation doctor diagnostic result will be coincident with the disease name to be decided into the image interpretation result certainty factor entry field 92. FIG. 18 shows the requested content properness factor entry field 91 and the image interpretation result certainty factor entry field 92 in which the properness factor of requested content and the certainty factor of image interpretation result have been entered. After entering the properness factor of requested content and the certainty factor of image interpretation result, the image interpretation doctor clicks the examination evaluation send button 93.

When the examination evaluation send button 93 is clicked, the image interpretation report creating apparatus 7 sends the image interpretation report ID (here, "300001"), finding (here, "liver kidney contrast high"), image interpretation doctor diagnostic result (here, "fatty liver"), image interpretation doctor name (here, "Fuji Taro"), properness factor of requested content (here, "3"), and certainty factor of image interpretation result (here, "3") to the examination information management apparatus 10 (step S53).

The image interpretation doctor examination evaluation information acquiring unit 22 of the examination information management apparatus 10 receives the image interpretation report ID (here, "300001"), finding (here, "high liver kidney contrast"), image interpretation doctor diagnostic result (here, "fatty liver"), image interpretation doctor name (here, "Fuji Taro"), properness factor of requested content (here, "3"), and certainty factor of image interpretation result (here, "3") from the image interpretation report creating apparatus 7 and outputs them to the examination information managing unit 24. The examination information managing unit 24 stores the record including the image interpretation report ID, finding, image interpretation doctor diagnostic result, image interpretation doctor name, properness factor of requested content, and certainty factor of image interpretation result in the image interpretation doctor examination evaluation information database (see FIG. 3) (step S71). FIG. 19 shows the image interpretation doctor examination evaluation information database in this case. As shown in FIG. 19, a new record including the above-mentioned information is added to the lowermost row of the image interpretation doctor examination evaluation information database. In this regard, the examination information managing unit 24 may inform the client doctor of the properness factor of requested content through an electronic mail or the like. Thereby, the client doctor may promptly know the properness factor of requested content requested by him- or herself. Further, when the properness factor of requested content is "1", the examination information managing unit 24 may inform the manager (hospital director) or the like.

Figure 20:
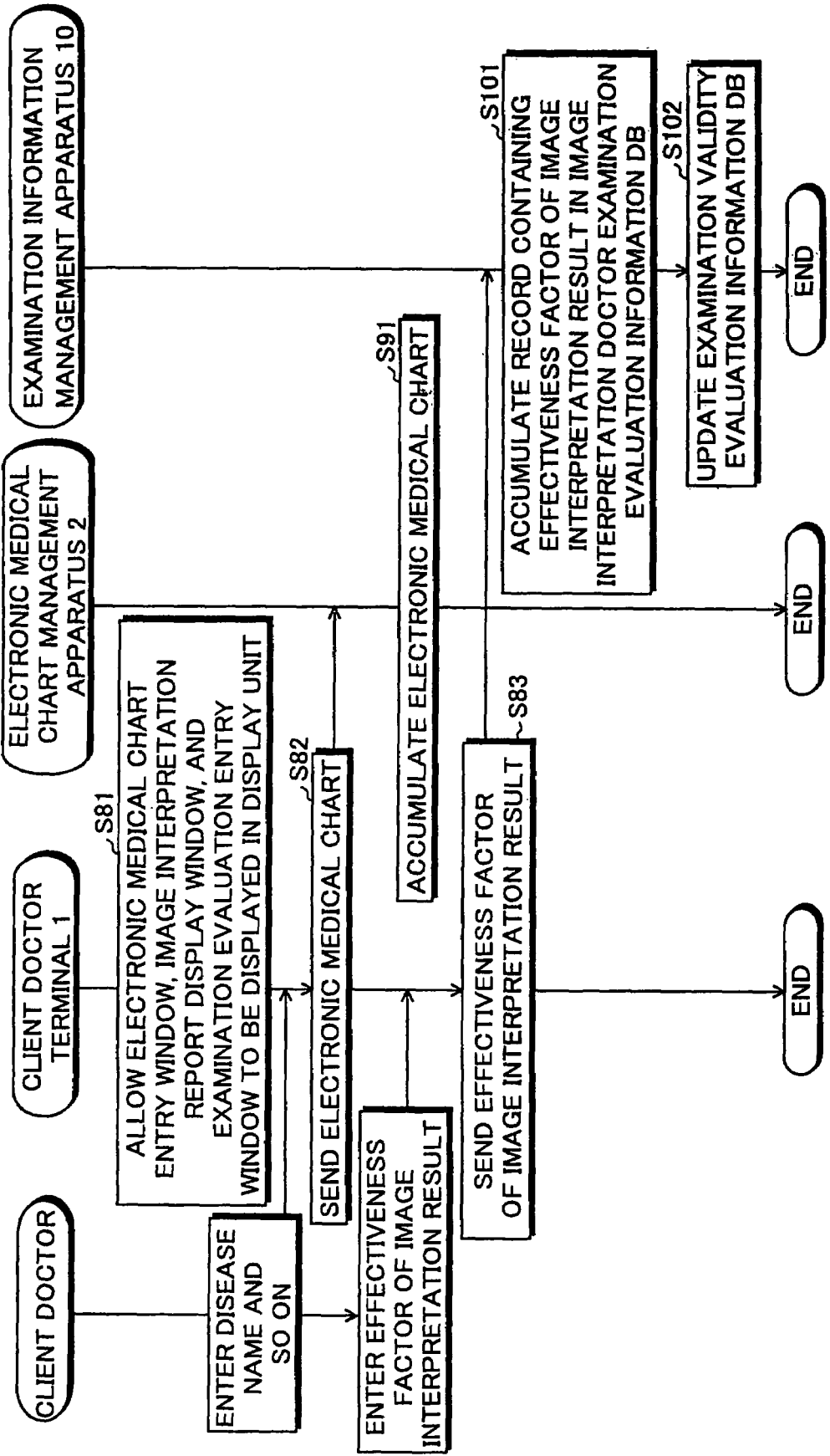
FIG. 20 is a flowchart showing an operation of the medical information management system shown in FIG. 1.

Next, an operation of the medical information management system when the client doctor makes a diagnosis (decides a disease name) will be explained with reference to FIG. 20. FIG. 20 is a flowchart showing the operation of the medical information management system when the client doctor makes a diagnosis.

Figure 21:
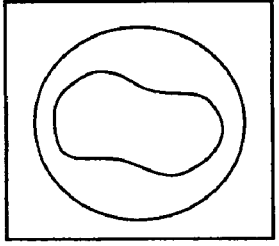

First, the client doctor terminal 1 causes the electronic medical chart entry window, an image interpretation report display window, and an examination evaluation entry window to be displayed in the display unit 1b (step S81). FIG. 21 shows the area 32 (FIG. 8) of the display screen of the display unit 1b of the client doctor terminal 1 in this case. As shown in FIG. 21, the electronic medical chart entry window 42, the image interpretation report display window 45, and the examination evaluation entry window 46 are displayed in the display unit 1b of the client doctor terminal 1.

The image interpretation report display window 45 contains an examination information display field 101, a finding display field 102, a diagnosis display field 103, and a key image display field 104. The examination evaluation entry window 46 contains a result effectiveness factor entry field 111 and an examination evaluation send button 112. The examination evaluation entry window 46 contains an image interpretation result effectiveness factor entry field 111 and the examination evaluation send button 112. In the examination information display field 101, the examination ID (here, "US1001"), examination type (here, "US"), a part to be examined (here, "abdomen"), patient name (here, "Yamada Saburo"), sex (here, "male"), age (here, "51"), imaging date (here, "May 15, 2006), and comments on the examination are displayed. In the key image display field 104, a key image is displayed. When the client doctor terminal 1 has a high-definition image monitor (viewer), a series of images obtained by the examination may be displayed on the viewer.

Figure 22:
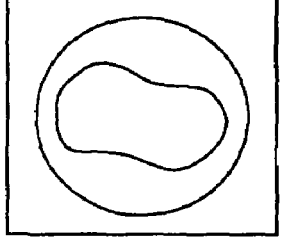

The client doctor makes a diagnosis by referring to the image interpretation report display window 45 and enters the diagnostic result (decided disease name), prescription, and so on in the second part 42 of the electronic medical chart entry window. FIG. 22 shows the second part 42 of the electronic medical chart entry window in which the diagnostic date (here, "May 16, 2006"), client doctor (diagnostic doctor) name (here, "Tanaka Ichiro"), and diagnostic result (here, "fatty liver") have been entered. After entering the diagnostic result and so on, the client doctor clicks the electronic medical chart save button 51.

When the electronic medical chart save button 51 is clicked, the client doctor terminal 1 sends the electronic medical chart to the electronic medical chart management apparatus 2 (step S82), and the electronic medical chart management apparatus 2 accumulates or updates the received electronic medical chart in the electronic medical chart database 2a (step S91).

Then, the client doctor enters the effectiveness factor of image interpretation result as the degree that the image interpretation result is effective for the diagnosis (here, "3") in the image interpretation result effectiveness factor entry field 111. FIG. 23 shows the area 32 (FIG. 8) of the display screen of the display unit 1b of the client doctor terminal 1 in this case. After entering the effectiveness factor of image interpretation result, the client doctor clicks the examination evaluation send button 112 within the examination evaluation entry window 46 with the mouse.

When examination evaluation send button 112 is clicked, the client doctor terminal 1 sends the image interpretation report ID and the effectiveness factor of image interpretation result to the examination information management apparatus 10 (step S83). The client doctor examination evaluation information acquiring unit 23 of the examination information management apparatus 10 receives the image interpretation report ID and the effectiveness factor of image interpretation result, and outputs them to the examination information managing unit 24. The examination information managing unit 24 accumulates the image interpretation report ID and the effectiveness factor of image interpretation result in the image interpretation doctor examination evaluation information database (see FIG. 4) (step S101). FIG. 24 shows the image interpretation doctor examination evaluation information database in this case. As shown in FIG. 24, a new record including the above-mentioned information is added to the lowermost row of the image interpretation doctor examination evaluation information database. In this regard, the examination information managing unit 24 may inform the client doctor of the effectiveness factor of image interpretation result through an electronic mail or the like. Thereby, the client doctor may promptly know the effectiveness factor of image interpretation result of the image interpretation result made by him- or herself. Further, when the effectiveness factor of image interpretation result is "1", the examination information managing unit 24 may inform the manager (hospital director) or the like.

Then, the examination information managing unit 24 updates the examination validity evaluation information database (step S102). Specifically, under the condition of a set of the examination content, the predicted disease name, and the prior certainty factor within the record that has been newly added at step S33 (here, the record in the lowermost row in FIG. 14), the examination information managing unit 24 calculates the average value of properness factors of requested content on plural examinations that match the condition, the average value of certainty factors of image interpretation result on the plural examinations that match the condition, and the average value of effectiveness factors of image interpretation result that match the condition. The method of calculating these three average values are explained as above. Then, the examination information managing unit 24 performs search in the examination validity evaluation information database (see FIG. 5) by using the predicted disease name, prior certainty factor, and examination content as search keys. Then, the examination information managing unit 24 writes the three average values acquired in the above manner in the fourth to sixth fields within the record obtained as a search result (here, the first record in FIG. 5), respectively, and rewrites them in the examination validity evaluation information database. Thus updated examination validity evaluation information database is used for the next examination request.

As described above, according to the embodiment, when the client doctor attempts to make an examination request, under the condition of a set of the examination content and the predicted disease name entered by the client doctor, the average value of properness factors of requested content on plural examinations that match the condition, the average value of certainty factors of image interpretation result on the plural examinations that match the condition, and the average value of effectiveness factors of image interpretation result that match the condition are displayed on the client doctor terminal 1, and thereby, the client doctor can select a more proper examination.

Further, when the properness factor of requested content entered by the image interpretation doctor is informed to the client doctor, the client doctor may know whether the examination requested by him- or herself is proper or not, and thereby, the skill of the client doctor can be improved.

Further, when the effectiveness factor of image interpretation result entered by the client doctor is informed to the image interpretation doctor, the image interpretation doctor may know whether the image interpretation performed by him- or herself is effective or not, and thereby, the skill of the image interpretation doctor can be improved.

Note that the examination information managing unit 24 may tally the properness factors of requested content with respect to each client doctor. This can be realized in the following manner. The examination information managing unit 24 performs search in the examination request information database (see FIG. 14) by using a certain client doctor name (e.g., "Suzuki Jiro") as a search key, and extracts plural records (the records in the second to sixth rows of FIG. 14). Then, the examination information managing unit 24 performs search in the image interpretation doctor examination evaluation information database (see FIG. 19) by using plural image interpretation report IDs within the extracted plural records as search keys. Then, the examination information managing unit 24 tallies the properness factors of requested content within the extracted plural records. Thereby, the properness factors of requested content on the examination requests of the client doctor "Suzuki Jiro" can be tallied. The above-mentioned processing may be executed on other client doctors.

Furthermore, the examination information managing unit 24 may inform the manager (hospital director or the like) of the tally result. Thereby, the manager (hospital director or the like) may grasp the skills of the client doctors.

Further, the examination information managing unit 24 may tally the effectiveness factors of image interpretation result with respect to each image interpretation doctor. This can be realized in the following manner, for example. The examination information managing unit 24 performs search in the image interpretation doctor examination evaluation information database (see FIG. 19) by using a certain image interpretation name (e.g., "Fuji Kuroto") as a search key, and extracts plural records (the records in the second, third, and seventh to ninth rows of FIG. 19). Then, the examination information managing unit 24 performs search in the client doctor examination evaluation information database (see FIG. 24) by using plural image interpretation report IDs within the extracted plural records as search keys. Then, the examination information managing unit 24 tallies the effectiveness factors of image interpretation result within the extracted plural records. Thereby, the effectiveness factors of image interpretation result on the image interpretation results of the image interpretation doctor "Fuji Kuroto" can be tallied. The above-mentioned processing may be executed on other client doctors.

Furthermore, the examination information managing unit 24 may inform the manager (hospital director or the like) of the tally result. Thereby, the manager (hospital director or the like) may grasp the skills of the image interpretation doctors.

In the embodiment, the prior certainty factor, the properness factor of requested content, the certainty factor of image interpretation result, and the effectiveness factor of image interpretation result are expressed by using values of "1" to "3", however, other values, characters, character strings may be used.

Next, a medical information management system including an examination information management apparatus according to the second embodiment of the present invention will be explained. FIG. 25 is a block diagram showing a configuration of the medical information management system including the examination information management apparatus according to the second embodiment of the present invention.

As shown in FIG. 25, the examination information management system includes a client doctor terminal 1, an electronic medical chart management apparatus 2, an examination issue apparatus 3, an examiner terminal 4, an imaging modality 5, an image server 6, an image interpretation report creating apparatus 7, an image interpretation report management apparatus 8, and an examination information management apparatus 150 according to the second embodiment of the present invention. These apparatuses may be connected to one another via a network such as LAN. Alternatively, the examination information management apparatus 105 may be directly connected to the client doctor terminal 1, the electronic medical chart management apparatus 2, the examination issue apparatus 3, the examiner terminal 4, the imaging modality 5, the image server 6, the image interpretation report creating apparatus 7, or the image interpretation report management apparatus 8.

In the embodiment, the examination issue apparatus 3 includes a recording medium for storing an examination history database 3a that accumulates examination history data as to examinations that have been performed in the past. FIG. 26 shows an example of the examination history database. As shown in FIG. 26, the examination history data contains examination ID, patient ID, examination type, examination content, and examination date. The examination ID is determined by the examination issue apparatus 3. The patient ID, examination type, and examination content are entered by the client doctor in the client doctor terminal 1. The examination date is entered by the examiner in the examiner terminal 4 or sent from the imaging modality 5 when the examination is performed in the imaging modality 5. The examination issue apparatus 3 may make a copy of the examination history database 3a as needed and send it to the examination information management apparatus 10, and the examination information management apparatus 10 may record the copied examination history database 3a in a hard disk 131.

The examination information management apparatus 150 includes a CPU 160, a memory 120, a hard disk control unit 130 with a hard disk 131, and a network interface 140. These are interconnected via a bus line. Further, the CPU 160 is connected to the network via the network interface 140.

Next, referring to FIG. 25, plural functional blocks configured by the CPU 160 and software (programs) will be explained. These functional blocks further include a contraindication information acquiring unit 28 in addition to the above explained examination request information acquiring unit 21, image interpretation doctor examination evaluation information acquiring unit 22, client doctor examination evaluation information acquiring unit 23, examination information managing unit 24, examination request prior information acquiring unit 25, examination content judging unit 26, and examination content validity outputting unit 27.

In the case where contraindication information is recorded in an electronic medical chart of a patient to be examined, the contraindication information acquiring unit 28 receives the contraindication information from the electronic medical chart management apparatus 2 and outputs it to the examination content judging unit 26. Otherwise, the contraindication information is sent from the electronic medical chart management apparatus 2 to the examination issue apparatus 3 in the case where the contraindication information is recorded in an electronic medical chart of the patient to be examined because it is necessary to cause the contraindication information to be displayed on the examiner terminal 4 to inform the examiner. Accordingly, the contraindication information acquiring unit 28 may receive the contraindication information of the patient to be examined not from the electronic medical chart management apparatus 2 but from the examination issue apparatus 3.

Figure 28:
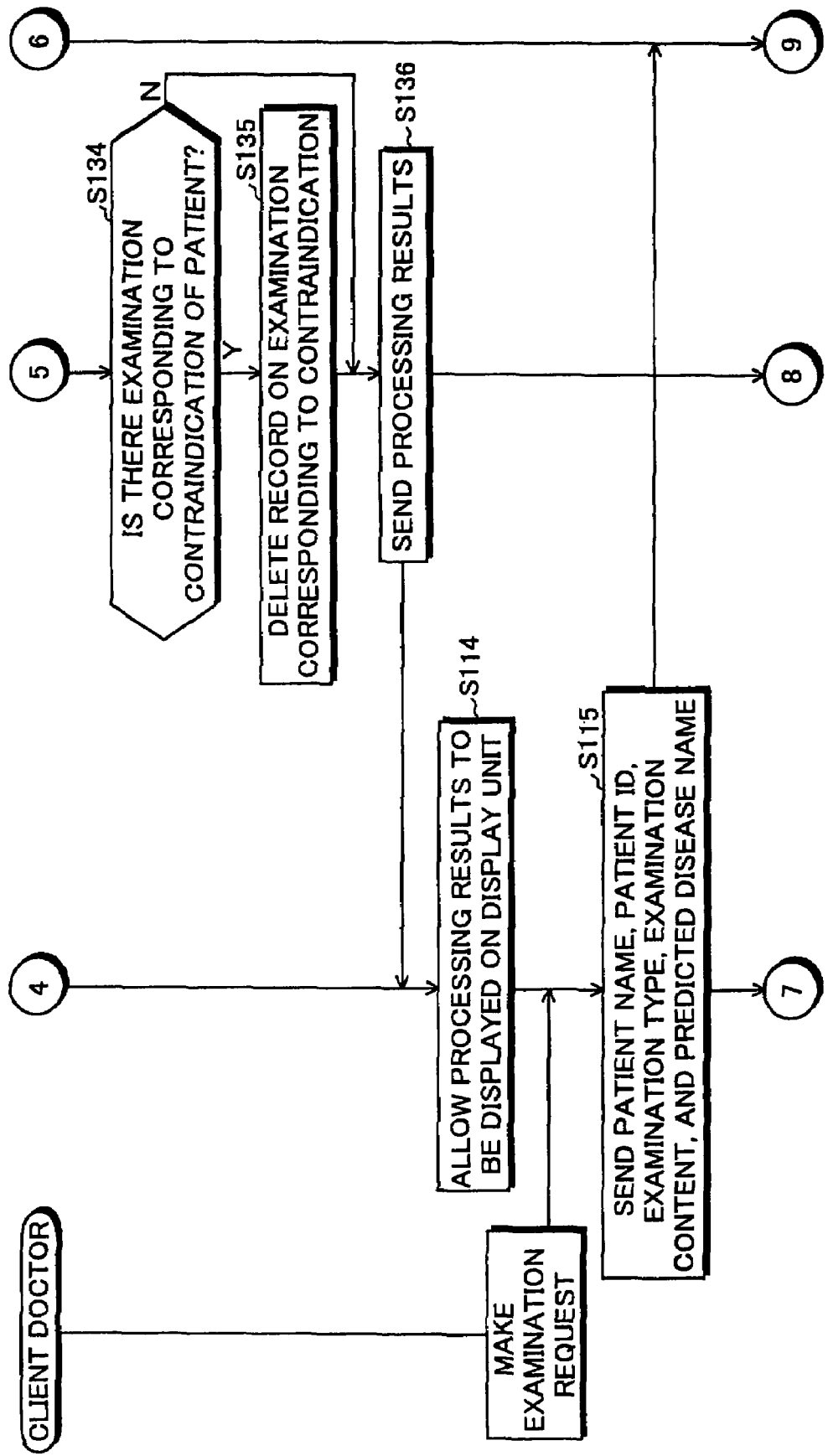
Figure 29:
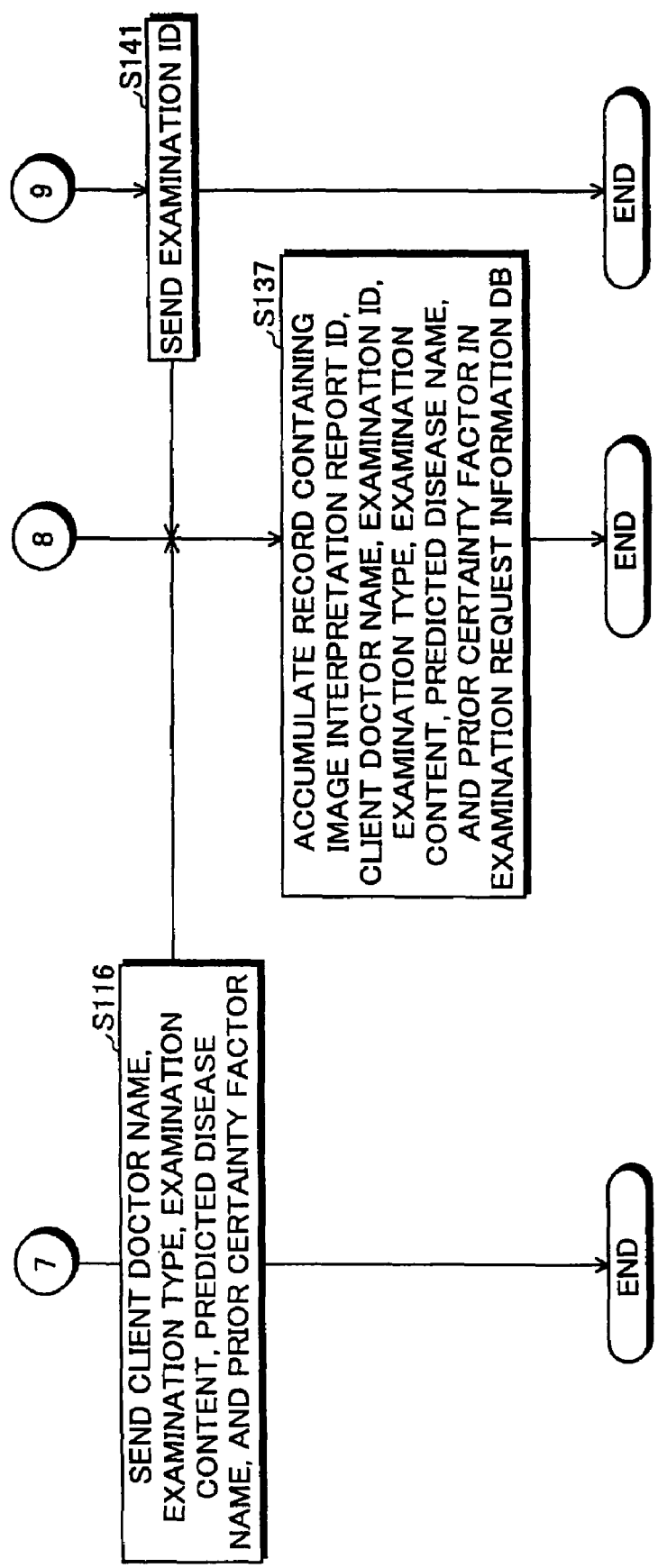

Next, an operation of the medical information management system according to the embodiment will be explained. FIGS. 27-29 are flowcharts showing the operation of the medical information management system when the client doctor makes an examination request.

First, the client doctor terminal 1 causes an electronic medical chart entry window, an examination request window, and an examination validity display window to be displayed in the display unit 1b (step S111). The display screen of the display unit 1b of the client doctor terminal 1 in this case are the same as those in FIGS. 8-10. The client doctor enters the patient name and so on in the first part 41 of the electronic medical chart entry window (see FIG. 9). For example, the patient name is "Sato Hanako", the patient ID is "000002", the patient sex is "female", and the patient age is "31".

The client doctor enters the consultation date (here, "May 15, 2006"), client doctor name (here, "Tanaka Ichiro"), patient symptoms (here, "lassitude", "swelling", and "jaundice"), finding based on the patient symptoms (here, "suspected to have fatty liver"), and the contraindication information (here, "during pregnancy, no radiographic examination") into the second part 42 of the electronic medical chart entry window. FIG. 30 shows the area 32 (FIG. 8) of the display screen of the display unit 1b of the client doctor terminal 1 in this case. After entering the patient symptoms and so on, the client doctor clicks the electronic medical chart save button 51 with a mouse.

When the electronic medical chart save button 51 is clicked, the client doctor terminal 1 sends the information of the electronic medical chart to the electronic medical chart management apparatus 2 (step S112), and the electronic medical chart management apparatus 2 accumulates the received information of the electronic medical chart in the electronic medical chart database 2a (step S121).

Figure 31:

Then, the client doctor decides the predicted disease name based on the patient symptoms. Here, the client doctor decides the predicted disease name as "fatty liver" based on the patient symptoms of "lassitude", "swelling", and "jaundice". Further, here, the client doctor judges that there is a high possibility that the diagnostic result (decided disease name) will be "fatty liver", that is, the prior certainty factor is "3". Furthermore, the client doctor attempts to make an examination request of examination content "abdominal US" for diagnosis of "fatty liver". Then, the client doctor enters the predicted disease name "fatty liver" into a predicted disease name entry field 61 within the examination request window 43, the prior certainty factor "3" into a prior certainty factor entry field 62, and the examination content to request "abdominal US" into an examination content entry field 63, respectively. FIG. 31 shows the area 32 (FIG. 8) of the display screen of the display unit 1b of the client doctor terminal 1 in this case. Then, the client doctor clicks a validity display button 64 within the examination request window 43 with the mouse.

When the validity display button 64 is clicked, the client doctor terminal 1 sends the predicted disease name, the prior certainty factor, and the examination content to the examination information management apparatus 150 (step S113). The client doctor terminal 1 may simultaneously send the contraindication information of the patient to the examination information management apparatus 150.

As is the case of the first embodiment, when receiving the predicted disease name, the prior certainty factor, and the examination content from the client doctor terminal 1, the examination request prior information acquiring unit 25 of the examination information management apparatus 150 outputs the received predicted disease name, prior certainty factor, and examination content to the examination content judging unit 26. The examination content judging unit 26 receives the predicted disease name, the prior certainty factor, the examination content, and soon from the examination request prior information acquiring unit 25 and outputs the predicted disease name, or the predicted disease name and the prior certainty factor to the examination information managing unit 24. The examination information managing unit 24 performs search in the examination validity evaluation information database (see FIG. 5) by using the predicted disease name, or the predicted disease name and prior certainty factor received from the examination content judging unit 26 as search keys (step S131). Here, the examination information managing unit 24 extracts the first to third records within the examination validity evaluation information database shown in FIG. 5 as search results because the predicted disease name is "fatty liver" and the prior certainty factor is "3". Then, the examination information managing unit 24 outputs the search results to the examination content judging unit 26.

Then, the examination content judging unit 26 makes a check of the patient (here, "Sato Hanako") as to whether an examination has been performed within a predetermined period (e.g., for the past three weeks or the like) or not (step S132). Whether an examination has been performed on a patient within a predetermined period or not can be checked in the following manner.

In the case where the copy of the examination history database 3a is recorded in the hard disk 131, the examination content judging unit 26 outputs the patient ID (here, "000002") to the examination information managing unit 24. The examination information managing unit 24 performs search in the copy of the examination history database 3a by using the patient ID received from the examination content judging unit 26 as a search key. Thus, whether or not an examination has been performed on a patient within a predetermined period can be checked.

On the other hand, in the case where the copy of the examination history database 3a is not recorded in the hard disk 131, the examination content judging unit 26 sends the patient ID directly or via the examination information managing unit 24 to the examination issue apparatus 3. The examination issue apparatus 3 performs search in the examination history database 3a by using the patient ID received from the examination information management apparatus 150 as a search key, and sends the search results to the examination information management apparatus 150. Thus, whether or not an examination has been performed on a patient within a predetermined period can be checked.

Here, since the patient ID is "000002", the second record within the examination history database shown in FIG. 26 is extracted as a search result in the examination information management apparatus 150 or the examination issue apparatus 3. The second record within the examination history database shown in FIG. 26 shows that the abdominal US examination was performed on the patient "Sato Hanako" corresponding to the patient ID "000002" on May 1, 2006.

Then, in the case where there is an examination that has been performed on the patient within the predetermined period, the examination content judging unit 26 deletes (filters) the records on the same examination content as the examination content of the examination from the search results in the validity evaluation information database obtained at step S131 (step S133). Here, since the abdominal US examination was performed on the patient "Sato Hanako" on May 1, 2006, the examination content judging unit 26 deletes the record containing the examination content "abdominal US" (the first record in FIG. 5) from the search results in the validity evaluation information database obtained at step S131 (the first to third records in FIG. 5). Thereby, the second and third records in FIG. 5 are left.

Then, the examination content judging unit 26 makes a check as to whether or not there is an examination corresponding to the contraindication of the patient (here, "Sato Hanako") in the processing result at step 131 or step S133 (here, the second and third records in FIG. 5) (step S134), and deletes the record on the examination (step S135) in the case where there is an examination corresponding to the contraindication of the patient. Here, since the contraindication information is "during pregnancy, no radiographic examination", the examination content judging unit 26 deletes the record containing the examination "abdominal CT" using radiography (the second record in FIG. 5). Thereby, only the third record in FIG. 5 is left.

Then, the examination content validity outputting unit 27 sends the processing result (here, the third record in FIG. 5) to the client doctor terminal 1 and causes it to be displayed in the client doctor terminal 1 (step S136). The examination content validity outputting unit 27 causes a warning to be displayed in the client doctor terminal 1 for notifying the client doctor that there is an examination that has been performed on the patient (here, "Sato Hanako") in the predetermined period and there is an examination corresponding to the contraindication.

The client doctor terminal 1 receives the processing results performed in the examination information management apparatus 10, and causes them to be displayed on the display unit 1b within the examination validity display window 44 (step S114). FIG. 32 shows the area 32 (FIG. 8) of the display screen of the display unit 1b of the client doctor terminal 1. As shown in FIG. 32, the warning "Abdominal US was already performed on patient 'Sato Hanako' on May 1, 2006." and the warning "Patient 'Sato Hanako' is in pregnancy, no radiographic examination is allowed for 'Sato Hanako'." are displayed. Furthermore, within the examination validity display window 44, the contents of the second record in FIG. 5 (the predicted disease name "fatty liver", the prior certainty factor "3", and the examination content "abdominal MRI", the factor of requested content "1.2", the certainty factor of image interpretation result "1.2", and the effectiveness factor of image interpretation result "1.8") are displayed. Referring to the examination validity display window 44 shown in FIG. 32, the client doctor may found that the abdominal US was already performed on the patient "Sato Hanako" on May 1, 2006, and the examination of examination content "abdominal CT" is not allowed. Then, the client doctor judges whether or not the doctor makes a request for the examination of the examination content entered in the examination content entry field 63 of the examination request window 43 (here, "abdominal US").

Figure 33:
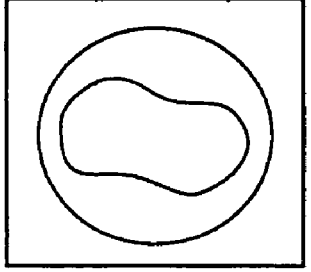
FIG. 33 shows an image interpretation report creation window displayed on the display unit of the client doctor terminal in FIG. 25.

In this regard, the client doctor may refer to the image interpretation report on the abdominal US that was performed on the patient "Sato Hanako" on May 1, 2006 by predetermined operation (e.g., pushing down the first function key or the like). For realization of the image interpretation report display, the client doctor terminal 1 sends the patient ID "000002" of the patient "Sato Hanako" to the image interpretation report management apparatus 8, and the image interpretation report management apparatus 8 performs search in the image interpretation report DB 8a by using the patient ID "000002" as a search key and sends search results to the client doctor terminal 1. FIG. 33 shows the image interpretation report display window 45 showing the image interpretation report on the abdominal US performed on the patient "Sato Hanako" on May 1, 2006. The image interpretation report display window 45 may be displayed as a new window in front of the first part 41 (FIG. 9) of the electronic medical chart entry window, the second part 42 (FIGS. 30-32) of the electronic medical chart entry window, the examination request window 43, and/or the examination validity display window 44, for example. The image interpretation report display window 45 shown in FIG. 33 shows that no abnormality was found in the abdominal US performed on the patient "Sato Hanako" on May 1, 2006. The client doctor may use the image interpretation report for deciding the examination request. Then, the client doctor may end the display of the image interpretation report display window 45 by performing predetermined operation (e.g., pushing down the second function key or the like).

In the case where the client doctor judges to make a request not for the examination of the examination content entered in the examination content entry field 63 of the examination request window 43 (here, "abdominal US"), but for the examination of the other examination content (e.g., "abdominal MRI") by referring to the image interpretation report on the abdominal US performed on the patient "Sato Hanako" on May 1, 2006, the doctor may enter the examination content in the examination content entry field 63 of the examination request window 43. In this regard, the client doctor may click the validity display button 64 again. In response, the client doctor terminal 1 executes steps S113 and S114 again, and the examination information management apparatus 150 executes steps S131-S136 again.

When the examination request button 65 is clicked, the client doctor terminal 1 sends the patient name (here, "Sato Hanako"), the patient ID (here, "000002"), the examination type (here, "MRI"), the examination content (here, "abdominal MRI"), and the predicted disease name (here, "fatty liver") to the examination issue apparatus 3 (step S115), and sends the client doctor name (here, "Tanaka Ichiro"), the examination type, the examination content, the predicted disease name, and the prior certainty factor (here, "3") to the examination information management apparatus 150 (step S116).

When receiving the patient name, the patient ID, the examination type, the examination content, and the predicted disease name from the client doctor terminal 1, the examination issue apparatus 3 determines the examination ID (here, "MRI002") and sends the determined examination ID to the examination information management apparatus 150 (step S141). The examination issue apparatus 3 causes the determined examination ID, the patient name, the patient ID, the examination type, the examination content, and the predicted disease name to be displayed in the examiner terminal 4. The examiner refers to the patient name and so on displayed in the display unit of the examiner terminal 4 and performs the examination in the imaging modality 5. When the examiner performs the examination, the examination issue apparatus 3 accumulates the record containing the examination ID, the patient ID, the examination type, the examination content, the predicted disease name, and the examination date (here, "May 15, 2006") in the examination history database (FIG. 26). FIG. 34 shows the examination history database in this case. As shown in FIG. 34, a new record containing the examination ID "MRI002", the patient ID "000002", the examination type "MRI", the examination content "abdominal MRI", the predicted disease name "fatty liver", and the examination date "May 15, 2006" is added to the lowermost row of the examination history database. On the other hand, the medical image data imaged in the imaging modality 5 is sent to the image server 6 and accumulated in the image database 6a. Further, the image interpretation report ID is determined in the image interpretation report management apparatus 8 and sent to the examination information management apparatus 10.

Note that the processing when the image interpretation doctor performs image interpretation and the processing when the client doctor makes a diagnosis in the medical information management system according to the embodiment are the same as those in the previously explained medical information management system according to the first embodiment.

As described above, according to the embodiment, since warnings on an examination performed on a patient in a predetermined period and an examination corresponding to the contraindication of the patient are displayed, and the properness factor of requested content, the certainty factor of image interpretation result, and the effectiveness factor of image interpretation result on the examination performed on the patient in the predetermined period and other examinations than the examination corresponding to the contraindication of the patient are displayed on the client doctor terminal 1, the client doctor can select a more proper examination.

The invention claimed is:

1. An examination information management apparatus connected directly or via a network to at least one client doctor terminal to be used when a client doctor requests an examination and at least one image interpretation report creating apparatus to be used when an image interpretation doctor creates an image interpretation report based on medical images obtained with respect to the examination requested by the client doctor, for managing information on the examination to support selection of examination by the client doctor, said apparatus comprising:

a storage unit for storing an examination evaluation database that accumulates evaluation information on plural examinations performed for plural predicted disease names in a past, said evaluation information including requested content properness factors representing evaluations made by the image interpretation doctor as to validity of the plural examinations in decision of a disease name, and image interpretation result certainty factors representing evaluations previously made by the image interpretation doctor as to a possibility that a disease name decided in the image interpretation report created by the image interpretation doctor will match the disease name to be decided later;

an examination information managing unit for managing the examination evaluation database;

an examination request prior information acquiring unit for acquiring examination request prior information including information representing a disease name predicted by the client doctor and an examination candidate for the predicted disease name from said client doctor terminal;

an examination content judging unit for causing said examination information managing unit to perform search in said examination evaluation database based on at least the predicted disease name, and acquiring evaluation information on the examination candidate for the predicted disease name based on the search performed by said examination information managing unit, said evaluation information including a requested content properness factor representing an evaluation made by the image interpretation doctor as to validity of the examination candidate in decision of a disease name, and an image interpretation result certainty factor representing an evaluation made by the image interpretation doctor as to a possibility that a disease name decided in the image interpretation report created by the image interpretation doctor will match the disease name to be decided later; and an examination content validity outputting unit for outputting the evaluation information acquired by said examination content judging unit to said client doctor terminal to cause said client doctor terminal to display the requested content properness factor and the image interpretation result certainty factor of the examination candidate for the predicted disease name.

2. The examination information management apparatus according to claim 1, further comprising:

an examination request information acquiring unit for acquiring, when the client doctor selects an examination to be requested, examination request information including information representing the disease name predicted by the client doctor and the examination selected by the client doctor;

a first evaluation information acquiring unit for acquiring, from said image interpretation report creating apparatus, first evaluation information on an evaluation made by the image interpretation doctor, who creates the image interpretation report based on the medical images obtained in the examination requested by the client doctor, as to the selection of the examination by the client doctor; and a second evaluation information acquiring unit for acquiring, from said client doctor terminal, second evaluation information on an evaluation made by the client doctor as to the image interpretation report created by the image interpretation doctor based on the medical images obtained in the examination requested by the client doctor;

wherein said examination information managing unit creates or updates the examination evaluation database based on the examination request information, the first evaluation information, and the second evaluation information.

3. The examination information management apparatus according to claim 2, wherein:

at least one of said examination request prior information and said examination request information further includes a prior certainty factor representing an evaluation previously made by the client doctor as to a possibility that the disease name predicted by the client doctor will match a disease name to be decided later;

said first evaluation information includes the requested content properness factor and the image interpretation result certainty factor; and said second evaluation information includes an image interpretation result effectiveness factor representing an evaluation made by the client doctor as to effectiveness of the image interpretation report created by the image interpretation doctor.

4. The examination information management apparatus according to claim 1, further comprising:

an examination content acquiring unit for acquiring information on a contraindication of a patient from an electronic medical chart management apparatus connected directly or via a network to said examination information management apparatus;

wherein said examination content judging unit gives a warning when judging the selected examination is an examination to be avoided for the patient based on information on the contraindication of the patient acquired by said examination content acquiring unit.

* * * * *